US006571793B1

(12) United States Patent
Nilsson

(10) Patent No.: US 6,571,793 B1
(45) Date of Patent: Jun. 3, 2003

(54) OPTIMIZATION OF AN ELECTROSTATICALLY DOSED DRY POWDER INHALER

(75) Inventor: Thomas Nilsson, Mariefred (SE)

(73) Assignee: Microdrug AG, Hergiswil (CH)

(*) Notice: Subject to any disclaimer, the term of this patent is extended or adjusted under 35 U.S.C. 154(b) by 63 days.

(21) Appl. No.: 09/688,697

(22) Filed: Oct. 17, 2000

(30) Foreign Application Priority Data

Sep. 21, 2000 (SE) .............................................. 0003364

(51) Int. Cl.[7] .............................................. A61M 15/00

(52) U.S. Cl. ............................ 128/203.15; 128/203.12; 128/203.27; 128/203.26; 239/693; 239/708; 239/338

(58) Field of Search ........................ 128/203.12, 203.15, 128/203.17, 203.26, 203.27, 202.25, 203.21, 200.14; 239/693, 708, 338

(56) References Cited

U.S. PATENT DOCUMENTS 5,522,385 A * 6/1996 Lloyd et al. ........... 128/200.14
5,839,430 A * 11/1998 Cama ..................... 128/200.14
5,848,587 A * 12/1998 King ...................... 128/200.14
6,003,512 A * 12/1999 Gerde .................... 128/203.15
6,012,450 A * 1/2000 Rubsamen ............. 128/200.14
6,024,090 A * 2/2000 Gonda et al. ........... 128/200.14
6,026,809 A * 2/2000 Abrams et al. ......... 128/200.22
6,041,777 A * 3/2000 Faithfull et al. ........ 128/200.24
6,076,522 A * 6/2000 Dwivedi et al. ........ 128/203.12
6,089,227 A * 7/2000 Nilsson .................. 128/203.12
6,142,146 A * 11/2000 Abrams et al. ......... 128/203.15
6,263,872 B1 * 7/2001 Schuster et al. ........ 128/203.26
6,309,671 B1 * 10/2001 Foster et al. ................ 424/434

* cited by examiner

*Primary Examiner*—Glenn K. Dawson
*Assistant Examiner*—Michael Mendoza
(74) *Attorney, Agent, or Firm*—Young & Thompson

(57) ABSTRACT

A method and a process are disclosed for optimizing an electrostatically dosed dry powder inhaler (EDPI) for utilization of a prepared pre-metered electro-dose consisting of a electro-powder. An arrangement is set-up for measuring parameters affecting a systemic delivery or local lung delivery of a pre-metered electro-dose from and DPI including analysis of dose de-agglomeration, particle size distribution as well as dose-to-dose variation together with pressures times and flows. A dry powder inhaler, DPI, is adjusted for a systemic or a local lung setting with respect to activation pressure and closing pressure having a DPI with a 20 to 60 liters/minute inhalation air flow for systemic delivery setting and 20 to 80 liters/minute for a local lung setting. Furthermore the de-agglomeration power is adjusted between 0.1 and 6 watts to be used in the DPI by optimizing the pressure drop and inhalation flow rate by changes to the mouthpiece and/or the device member and their relation to each other. The DPI activation pressure is further adjusted to a value between 0.5 and 4 kPa and closing pressure between 0.5 and 4 kPa to eliminate the low power at the start and end of the inhalation. The method and process then verify that the DPI meets the specifications set regarding de-agglomeration of power and opening and closing pressures together with timings within the DPI active time. Furthermore is verified that de-agglomeration difference, expressed in percent using an expression $100[1\text{-de-agglomeration}(Q_{1\ kPa})/\text{de-agglomeration}(Q)]$, is not more than 50%. Finally if the DPI is not approved as an EDPI the tested DPI and/or electro-dose is further adjusted to check if the DPI can meet the specifications of an EDPI.

28 Claims, 21 Drawing Sheets

List of EDPI features

- Breath actuated
- Continuous dosing
- Asthma/System delivery
- Flow/Pressure setting
- Inhalation time
- Material choice
- Electrical
- Electro-powder particle size distribution
- Flow velocity at mouthpiece exit

Fig. 22

OPTIMIZATION OF AN ELECTROSTATICALLY DOSED DRY POWDER INHALER

TECHNICAL FIELD

The present invention relates to administration of medical powders into the respiratory tract by releasing an electrostatically dosed powder to be inhaled and more particularly to a method for optimizing the function of an electrostatically dosed dry powder inhaler (EDPI) in relation to a pre-metered dose of electro-powder.

BACKGROUND

Dosing of drugs is carried out in a number of different ways in the medical service today. Within health care more and more is focused on the possibility of dosing medical drugs as a powder directly to the airways and lungs of a user by means of an inhaler in order to obtain an effective, quick and user-friendly administration of such substances. But today the dosing quality is not good enough to be used for wide range of drugs. This is specially the case for systemic delivery by inhalation through a dry powder inhaler (DPI) which represents an important segment making it possible to compete with the injection needle for many types of drugs, i.e. insulin, pain management etc.

A dry powder inhaler of today, (DPI), represents a device intended for administration of powder into the deep or upper lung airways by oral inhalation. With deep lung should be understood the peripheral lung and alveoli, where direct transport of active substance to the blood can take place. Particle sizes, to reach into the deep lung, should be in a range 0.5–3 μm and for a local lung delivery in the range 3–5 μm. A larger grain size will easily stick in the mouth and throat, and a smaller grain size may accompany the expiration air out again.

To succeed with systemic delivery of medical powders to the deep lung by inhalation there are some criteria, which have to be fulfilled. The most important is a very high degree of de-agglomeration of the medical powder but also an exact dose is of great importance. This is not possible with dry powder inhalers of today without special arrangements as for example a so-called spacer.

By means of a spacer the small grains are evenly distributed in a container from which the inhalation can take place. Upon inhalation from the spacer the fine powder is floating free in the air and will effectively reach the alveoli's of the lung. This method in principle has two drawbacks, firstly difficulties to control the amount of medicine emitted to the lung as an uncontrolled amount of powder sticks to the walls of the spacer and secondly difficulties in handling the relatively space demanding apparatus. It is also common to utilize carriers i.e. Lactose having a larger grain size onto which the fine power is distributed. Upon inspiration the large size grains will then stick in the oral cavity while the fine particle fraction, this is powder smaller than 5 μm, will be let free and proceed to the lung. For instance U.S. Pat. No. 5,642,727 discloses a tribo-inhaler having a container portion for electrostatically retaining a predefined dose of medicament powder. The container portion contains a plurality of polymeric beads that have diameters of approximately 50 to 200 microns. Each of the polymeric beads has a specific quantity of dry powder medicament electrostatically adhered to its surface.

An American document U.S. Pat. No. 5,871,010 addresses an inhaler apparatus with modified surfaces for enhanced release of dry powders. The inhaler apparatus disclosed comprises interior surfaces having low surface energy for minimizing contact between a medicament and the surfaces of the inhaler to minimize deposition of the dry powder.

Powders for inhalers have a tendency of agglomerating, in other word to clod or to form small or larger lumps, which then have to be de-agglomerated. De-agglomeration is defined as breaking up agglomerated powder by introducing electrical, mechanical, or aerodynamic energy. Usually de-agglomeration is performed as a stage one during dosing and as a final stage two during the user's inspiration through the DPI.

Inhaler devices normally use the force exerted by the user's more or less normal inspiration effort for de-agglomerating the medical substance administered when inhaling in an effort to bring as much as possible of the active substance into the lungs. This often leads to inhaler designs using high pressure drops, which will put the user's lungpower to the test.

Technologies to de-agglomerate today include advanced mechanical and aerodynamic systems and combinations between electrical and mechanical filling systems that can be seen in for instance in U.S. Pat. No. 5,826,633. Further there are systems disclosed for dispersing aerosolized doses of medicaments, e.g. U.S. Pat. Nos. 5,775,320, 5,785,049, and 5,740,794. Furthermore, in our International Publications WO 00/06236 and WO 00/06235 principles for de-agglomeration and classification are disclosed.

To meet some of these demands an electrostatic dosing of the powder onto a technical means for example a cassette can be done. An electrostatic dosing onto a device member or cassette was described in our Swedish Patent No. 9802648-7 (SE512 433) and the quality can be improved by utilizing the possibility to classify coarse particles larger than 5 μm to leave those out and dose only fine particles (less than 5 μm) onto the device member or cassette as described in our Swedish Patent No. 9802649-5 (SE512 386).

The term electro-powder refers to a micronized medical powder presenting controlled electrostatic properties to be suitable for electrostatic administration in an inhaler device. Such an electro-powder provides possibilities for a better dosing from electrostatically operating equipment such as disclosed in our U.S. Pat. No. 6,089,227 as well as our Swedish Patents No. 9802648-7 and 9802649-5, which present excellent inhalation dosing performance.

One major problem is to obtain a low relative standard deviation (RSD) between doses with this type of technique due to lack of in line control possibilities in production making it hard to be in compliance with regulatory demands. For electrostatically dosed medical substances the relative standard deviation between doses (RSD) should preferably be not more than <5%. For a prior art DPI the fine particle fraction and uniformity of dose together with the user dependency is a major drawback and this can be seen in a document by D. Prime, A. C. Grant, A. L. Slater and R. N. Woodhouse, "A Critical Comparison of the Dose Delivery Characteristics of Four Alternative Inhalation Devices Delivering Salbutamol: Pressurized Metered Dose Inhaler, Diskus Inhaler, Diskhaler Inhaler, and Turbuhaler Inhaler", Journal of Aerosol Medicine, Volume 12, Number 2, 1999, pp 75–84, Mary Ann Liebert, Inc.

Devices of prior art technology does often not reach a sufficiently high degree of de-agglomeration and an exact dose is not well developed and leaves much to be desired when it comes to dosage conformity and lung deposition effectiveness of the medical substance.

This means there is still a demand for a dry powder inhaler in which the important functions have been optimized to give a very high de-agglomeration, meaning a high fraction of particles under 5 $\mu$m for local lung and under 3 $\mu$m for deep lung and a uniformity of dose that is independent of minor variations in the user's inhalation.

SUMMARY

A method and a process are disclosed for optimizing an electrostatically dosed dry powder inhaler (EDPI) for utilization of a prepared pre-metered electro-dose consisting of a electro-powder. An arrangement is set-up for measuring parameters affecting a systemic delivery or local lung delivery of a pre-metered electro-dose from and DPI including analysis of dose de-agglomeration, particle size distribution as well as dose-to-dose variation together with pressures times and flows. A dry powder inhaler, DPI, is adjusted for a systemic or a local lung setting with respect to activation pressure and closing pressure having a DPI with a 20 to 60 liters/minute inhalation air flow for systemic delivery setting and 20 to 80 liters/minute for a local lung setting. Furthermore the de-agglomeration power is adjusted between 0.1 and 6 watts to be used in the DPI by optimizing the pressure drop and inhalation flow rate by changes to the mouthpiece and/or the device member and their relation to each other. The DPI activation pressure is further adjusted to a value between 0.5 and 4 kPa and closing pressure between 0.5 and 4 kPa to eliminate the low power at the start and end of the inhalation. The method and process then verify that the DPI meets the set specification regarding de-agglomeration power and opening and closing pressures. Furthermore is verified that de-agglomeration difference, expressed in percent using an expression 100[1−de-agglomeration($Q_{1\ kPa}$)/de-agglomeration(Q)], is not more than 50%. Finally if the DPI is not approved as an EDPI the tested DPI and/or electro-dose is further adjusted to check if the DPI can meet the specification of an EDPI.

SHORT DESCRIPTION OF THE DRAWINGS

The invention, together with further objects and advantages thereof, may best be understood by making reference to the following description taken together with the accompanying drawings, in which:

FIG. 22 demonstrates a list of EDPI features.

DESCRIPTION

Figure 1:
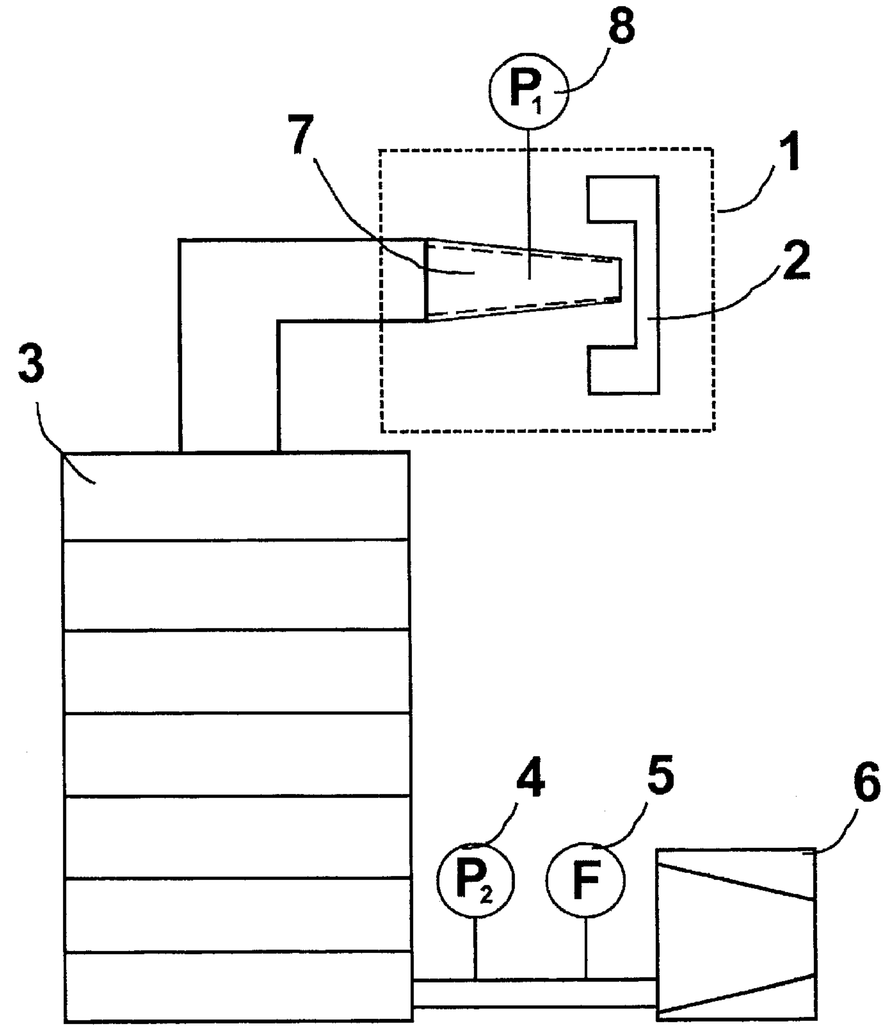
FIG. 1 shows a measurement set-up used for a measurement of size distribution and mass and further calculation of de-agglomeration and flow rate.

An EDPI is a DPI optimized for local or systemic delivery of a metered electro-dose of 1 $\mu$g to 2 mg of an electro-powder and presenting a dose de-agglomeration DD5 $\mu$m and DD3 $\mu$m of more than 25% together with a de-agglomeration difference measured according to USP compared with the de-agglomeration at a flow representing a pressure drop over the inhaler device reduced to 1 kPa (1−[de-agglomeration($Q_{1\ kPa}$)/de-agglomeration(Q)]×100) <50% and more preferably less than 25% and most preferably less than 10% and conform to the uniformity of dose stipulated in the USP. The uniformity of dose is expected to be between 90 and 110% and more preferable to be between 95% and 105%. By USP is referred to_USP 24-NF 19 Supplement 601 Aerosols/Physical Tests, pages 2674–2688.

The EDPI can be a single or multi-dose EDPI with or without electrical assistance for the operation. The DPI activation at a set inhalation pressure can be established by mechanical valves or by, e.g., an electrical sensor for sound or pressure and the closing of operation by a computer controlled timer or by a mechanical end point detection.

Particularly important is user independent particle size distribution and uniformity of dose. Measurements of these two properties are illustrated in an example of a de-agglomeration and mass measurement set-up in FIG. 1, where the DPI 1 to be optimized is used to determine the particle size distribution and mass from a pre-metered electro-dose sucked up from the device member 2 through a mouthpiece 7 using an Andersen Impactor 3 to determine the aerodynamic particle size distribution. The total pressure drop over the de-agglomeration set-up is measured with a pressure gauge 4 and the flow-rate of the air is measured with a flow-meter 5 in liters/minute. Suction may be achieved by means of a pumping device 6 including components to control flow and pressure.

All measurements of the particle size distribution are measured at least two different pressure drops over the inhaler device. At least all measurements are performed according to USP and then the pressure is changed for the measurement at a lower pressure 1 kPa over the inhaler device 1 in point 8.

The complementary particle size distribution is measured at 1 kPa pressure drop over the DPI 1 indicated by the pressure gauge 8 as differential pressure to the atmosphere and then the obtained flow-rate is noted down and named $Q_{1\ kPa}$. The particle size distribution obtained at the flow-rate $Q_{1\ kPa}$ is then compared with the particle size distribution obtained at the flow rate $Q_a$ meaning the flow rate obtained by using all other settings according to the USP.

Figure 17:
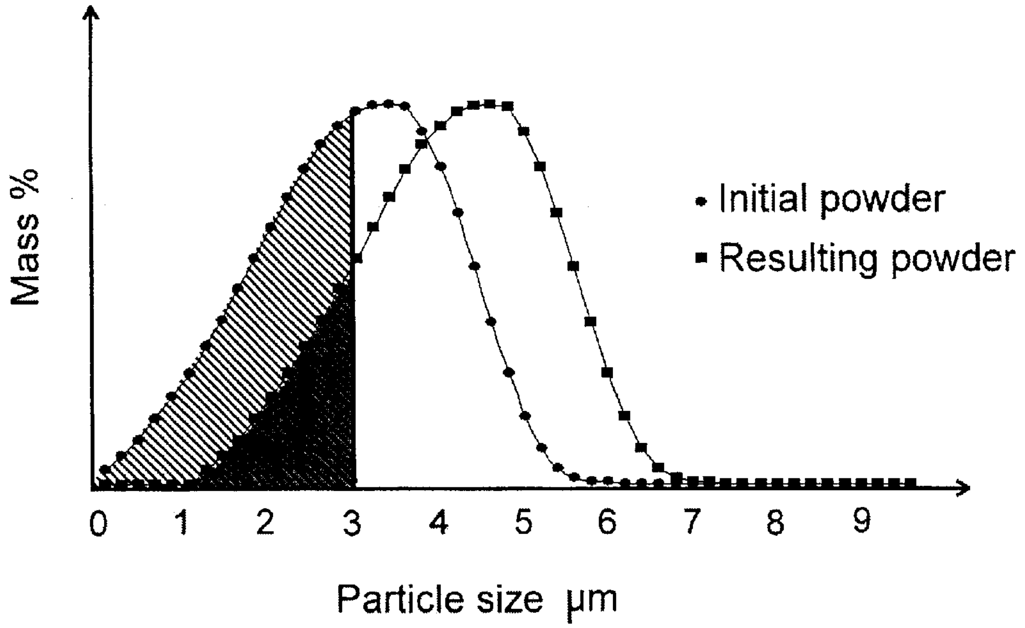
FIG. 17 is a graph representing calculation of de-agglomeration for particles up to 3 micrometers from an initial electro-powder particle size.
Figure 18:
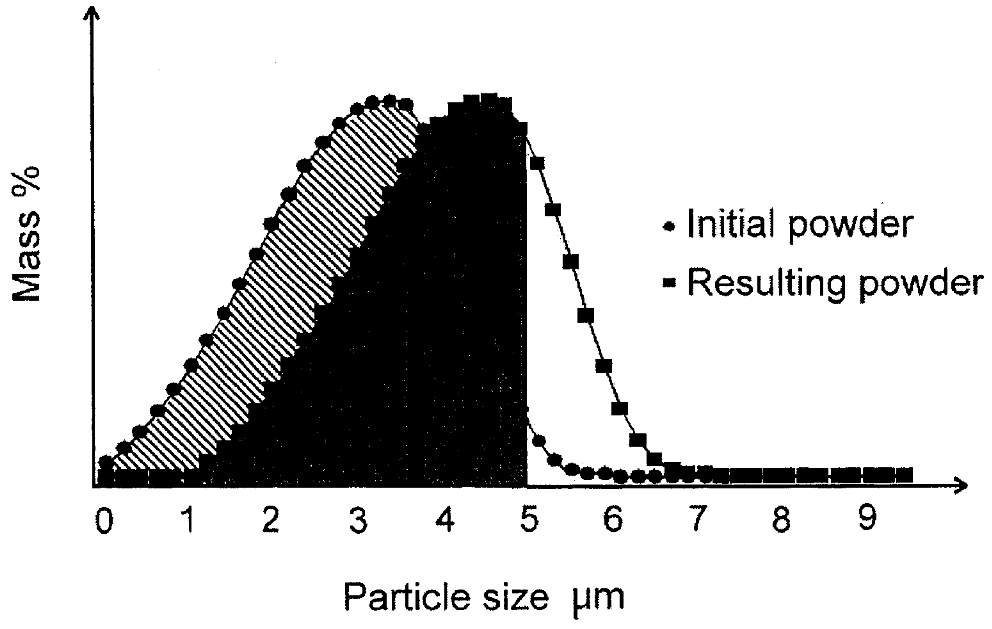
FIG. 18 is a graph representing calculation of de-agglomeration for particles up to 5 micrometers from an initial electro-powder particle size.

The results of the de-agglomeration tests at two different pressures over the inhaler device and compared according to FIGS. 17 and 18 to determine if the results meets the specification for an EDPI and also if the de-agglomeration for 3 and 5 μm, DD3 μm and DD5 μm are within the specifications for the intended application EDPI and medical drug.

The DD3 μm is used to optimise the EDPI for systemic delivery and the DD5 μm is used for optimising for local lung delivery when this reflects the quality of the de-agglomeration in the particle size range important for the local and deep lung delivery of the electro-power.

A metered electro-dose is here defined as a dose formed from an electro-powder constituting an active powder substance or a dry powder medical formulation, which is metered onto a device member forming a dose carrier, a metered dose having a fine particle fraction (FPF) presenting of the order 50% or more of its content with a particle size between 0.5–5 μm, the dose further presenting an optimized porosity of 75 to 99.9%. Where porosity is defined as $Dp_{electro\text{-}dose}=100-100(density_{electro\text{-}dose}/density_{electro\text{-}powder})$.

The electro-powder is defined as a medical powder intended for electrostatic dosing, formed of an active powder substance or dry powder medical formulation having a fine particle fraction (FPF) with 50% or more of particles between 0.5–5 μm and providing electrical specification measured at room temperature with an absolute specific charge of the order of 0.1 to 25 μC/g ($0.1\times10^{-6}$–$25\times10^{-6}$ Coulomb/gram of negative or positive charge) and desired to present a charge decay constant $Q_{50}$ of >0.1 sec, where $Q_{50}$ is defined as the time until 50% of the electrostatic charge is discharged, (for instance after a corona charging in an Electrical Low Pressure Impactor (ELPI) model 3935 from DEKATI LTD) and having a tap density of less than 0.8 g/ml and a water activity $a_w$ of less than 0.5. Water activity $a_w$ is a dimensionless quantity, which may, for instance, be measured with an AquaLab model series 3 TE. Tap density is, for instance, measured by using a Dual Autotap from Quantachrome© Corporation according to British Pharmacopoeia for Apparent Volume method. Both water activity and tap density are quantities well know to a person skilled in the field of chemistry analysis.

Particles intended for the deep lung, here defined as the peripheral lung and alveoli, where direct transport of an active substance to the blood can take place, should have a particle size in the range 0.5–3 μm. For treatment in the local lung, defined as upper parts of the lung, where treatment normally takes place for instance in asthma treatment, the particle size should be in the range 3–5 μm. All particle sizes are defined as the size of the particles measured with for instance a laser diffraction instrument e.g. a Malvern Mastersizer for physical size classification or an Andersen Impactor for an aerodynamic size classification and if not stated otherwise always referred to as aerodynamic particle size and measured according to USP.

A powder having a very fine particle fraction (FPF) must be prepared as it is generally only particles between 0.5 and 3 μm that will be medically active by being transported to the deep lung. For local lung treatments by inhalation the particle size should be between 3–5 μm.

A correct dose and a low dose-to-dose relative standard deviation (RSD) must be released from the inhaler. For electrostatically dosed dry powders with electrostatic properties inside set specification the relative standard deviation between doses (RSD) will not be more than 5%.

Many active substances will be of interest to use for local lung delivery or systemic delivery. The active substance is generally a pharmaceutical active chemical or biological substance intended for administration into the deep or upper lung airways by oral inhalation from the DPI.

Figure 2:
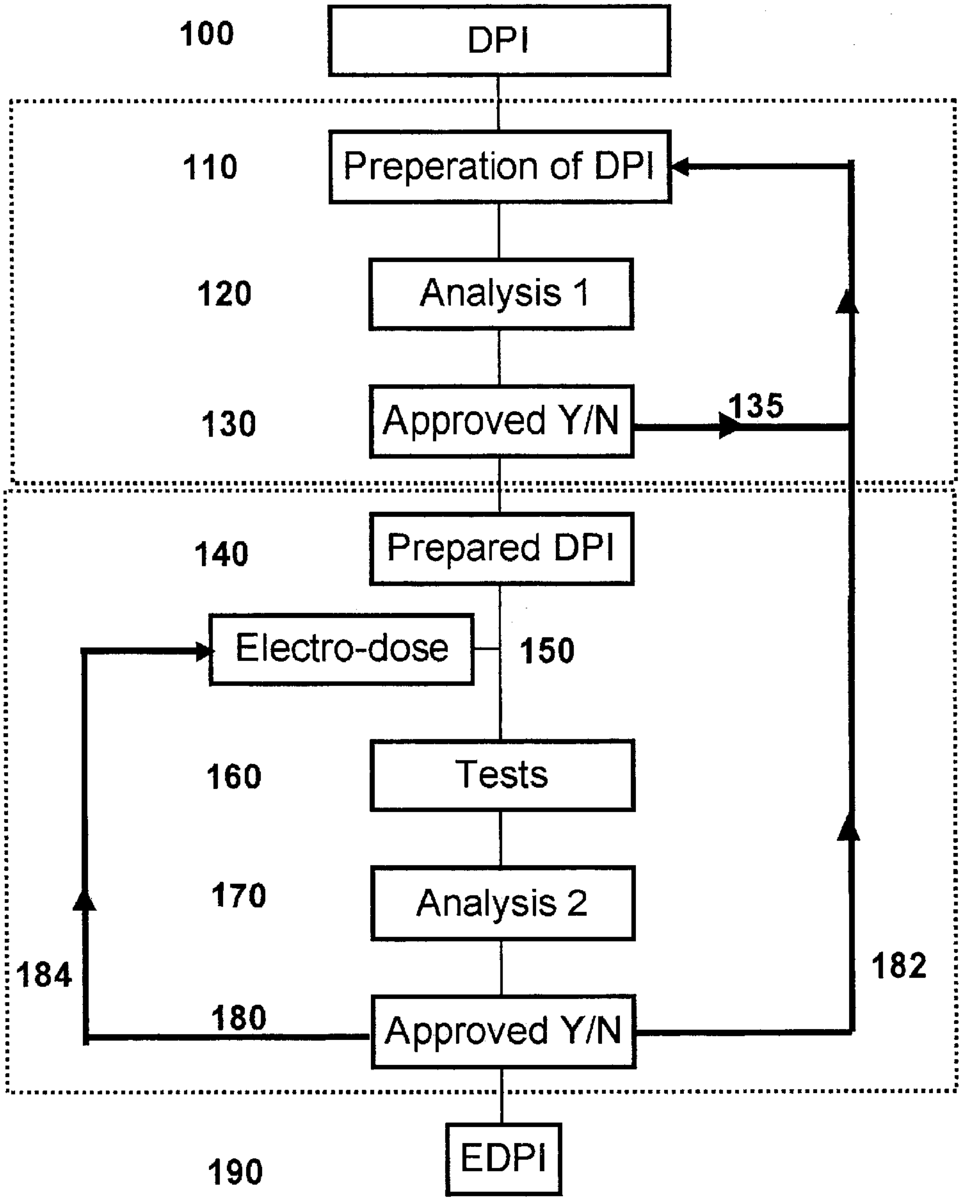
FIG. 2 is a summary flow chart illustrating preparation of the DPI for obtaining an electrostatically dosed dry powder inhaler, EDPI.
Figure 3:
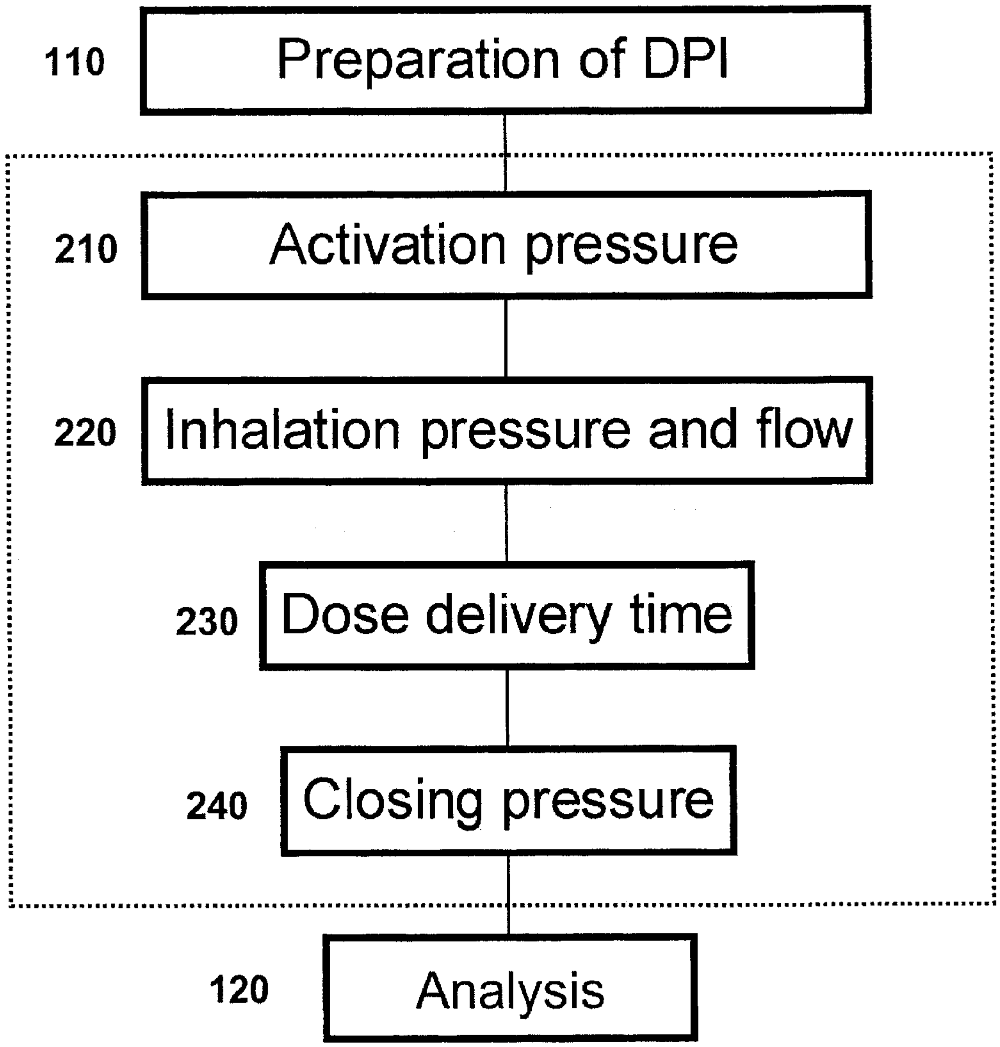
FIG. 3 is a summary flow chart illustrating preparation of the DPI.
Figure 4:
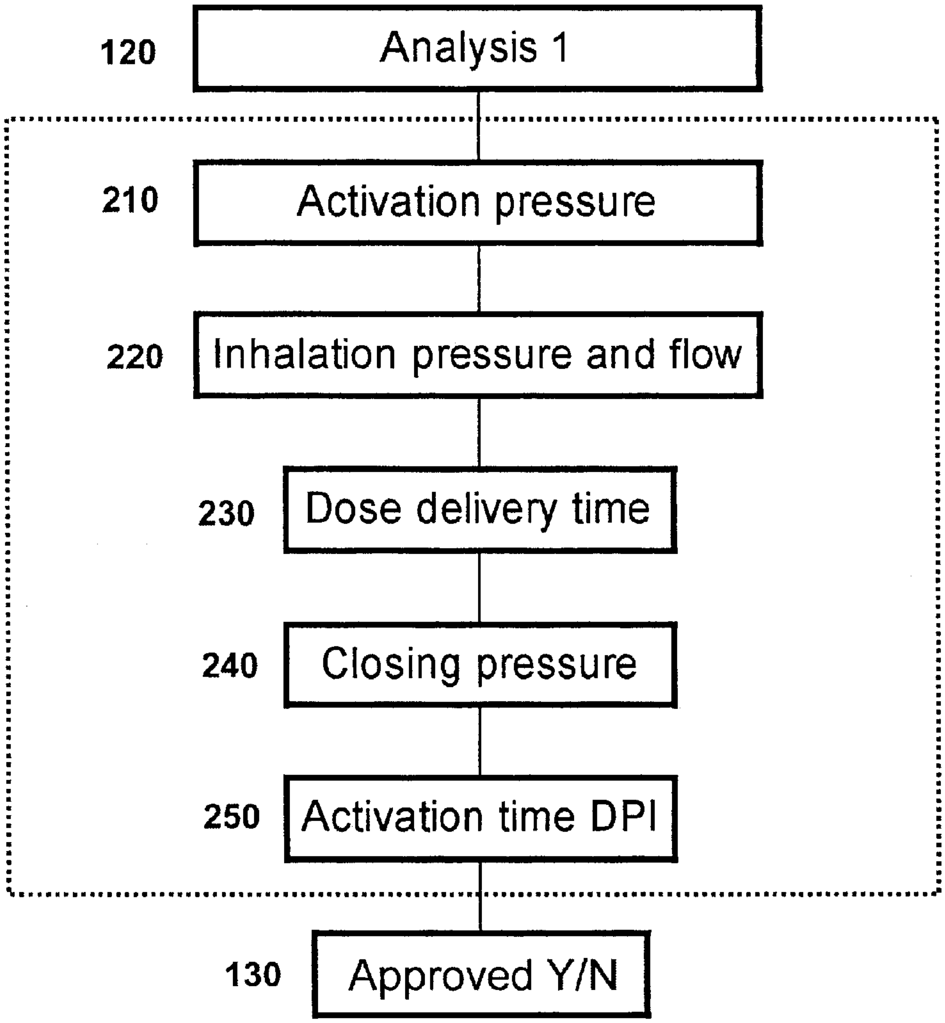
FIG. 4 is a summary flow chart illustrating a first analysis 1.
Figure 5:
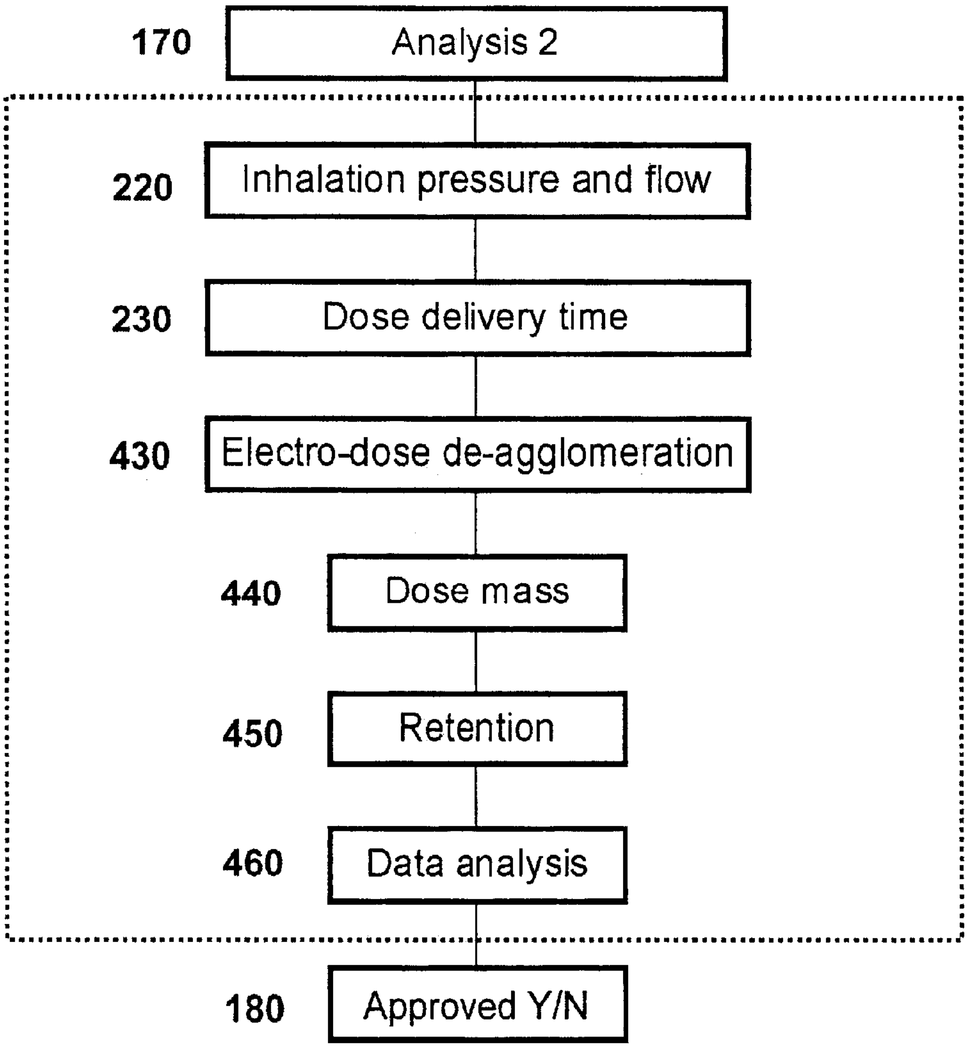
FIG. 5 is a summary flow chart illustrating a second analysis 2.
Figure 6:
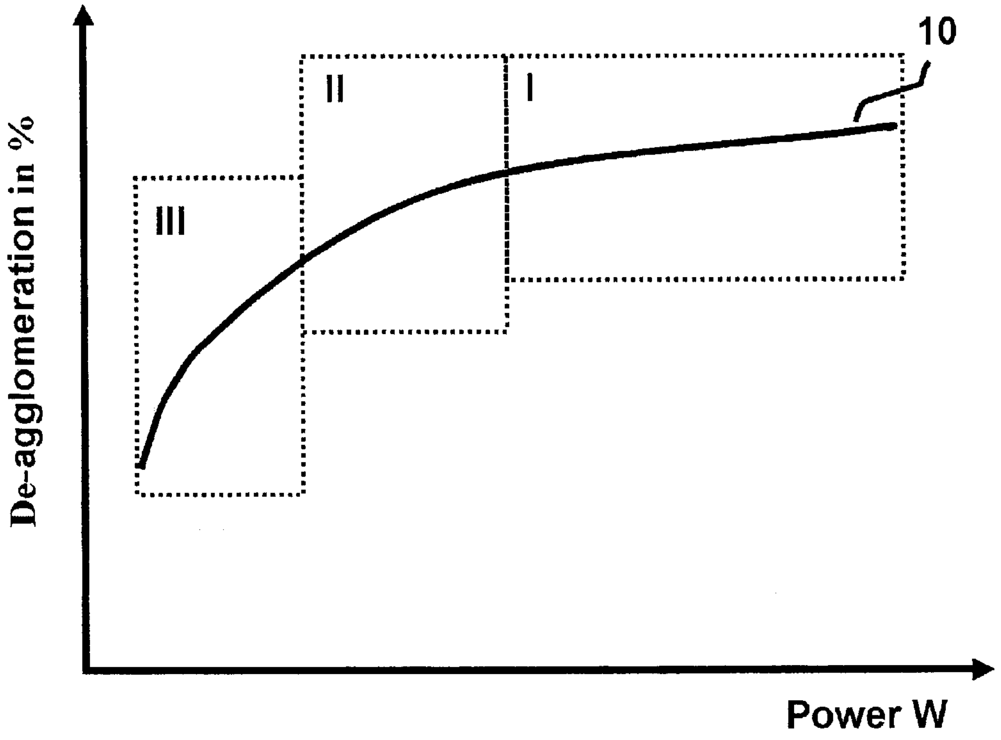
FIG. 6 illustrates the degree of de-agglomeration versus power in watts for an electro-dose.
Figure 7:
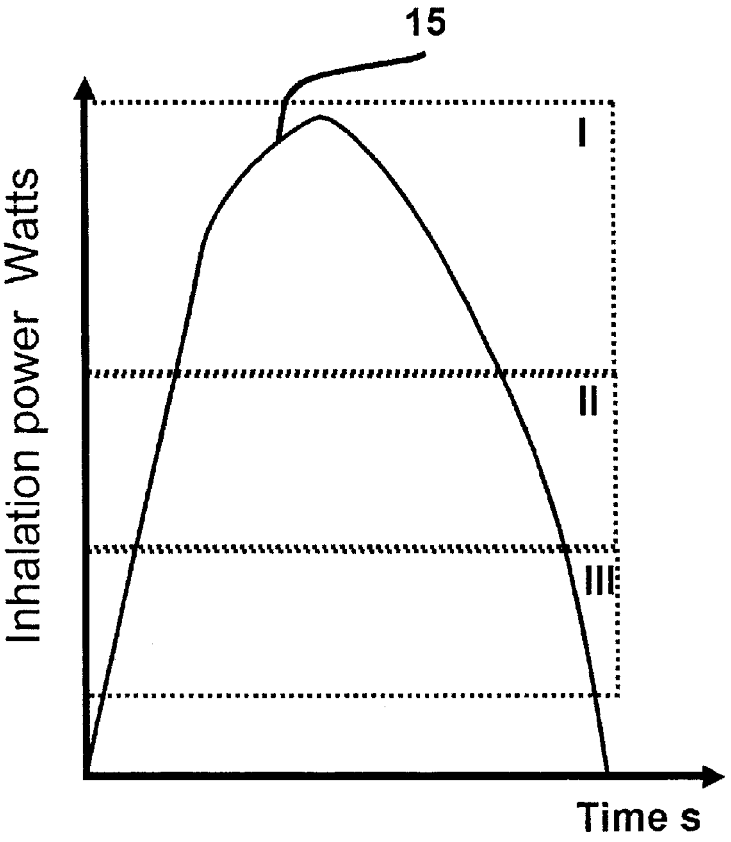
FIG. 7 illustrates the inhalation power in watts versus time in seconds.

Optimization of the intended DPI starts in step 100 of FIG. 2 by defining a device intended for delivering a de-agglomerated electro-dose consisting of an electro-powder into the deep lung for systemic delivery or delivery to the upper lung airways for local lung treatments. The process is advanced into step 110 for preparation of the DPI. The step 110 for preparation of the DPI further illustrated in FIG. 3 is then started with adjustment of a proper activation pressure in a step 210. The activation pressure step 210 is determined after considering FIG. 6 showing the amount of de-agglomeration 10 in % at different power levels measured in watts according to FIGS. 17 and 18 where the electro-dose being loaded into the DPI is defined as an electrostatically dosed electro-powder possessing the following specification: Porosity defined as $Dp_{electro\text{-}dose}=100-100(density_{electro\text{-}dose}/density_{electro\text{-}powder})>75\%$ and having an optimized de-agglomeration of >25%, and preferable being more than 50% and most preferable more than 75% and meeting a dosage uniformity according to USP 24-NF 19 Supplement 601 Aerosols/Physical Tests pages 2674–2688 and also meeting the Guidance for Industry Metered Dose Inhaler (MDI) and Dry Powder Inhaler (DPI) Drug Products Chemistry, Manufacturing, as well as Controls Documentation and Guidance for Industry Container Closure Systems for Packaging Human Drugs and Biologics and times measured with a calibrated chronograph, which will hereafter be referred to as USP, and also possessing a de-agglomeration difference measured according to USP compared with the de-agglomeration at a flow representing a pressure drop over the inhaler device reduced to 1 kPa $100\times(1-(\text{de-agglomeration}(Q_{1\ kpa})/\text{de-agglomeration}(Q))$ <50% and more preferably less than 25% and most preferably less than 10%.

In FIG. 6 the area I indicates an energy level enough for a controlled de-agglomeration of the electro-dose when the difference over a wide range of energy is giving a high degree of de-agglomeration. If the energy level for the operation of the DPI is chosen to be within the area II a more uncontrolled de-agglomeration will occur and careful consideration must be made if this is a correct design of the DPI.

Area III shows when the energy level of the de-agglomeration test is not enough and the result is very unpredictable showing a very big difference from a small difference in inhalation effect.

The activation pressure at step 210 should then normally be set within FIG. 6 area I or II to have a safe design specification for the combination of electro-dose and DPI setting. Activation pressure at step 210 is measured using a pressure gauge to determine at what inhalation pressure normally between 1 and 4 kPa the DPI starts to be active, i.e. when the intended DPI in step 100 is going from a ready to a stage when the electro-dose is starting to be de-agglomerated into the mouthpiece and inhaled.

After that the activation pressure in step 210 has been set the inhalation pressure and flow of step 220 is adjusted to obtain the correct effect for de-agglomeration, according to FIG. 6, during the inhalation through the DPI. When setting the inhalation pressure and flow at step 220 it must be realized that the effect during the inhalation is achieved as a function of the inhalation airflow and the pressure drop.

The pressure drop of the DPI is the total pressure drop over the DPI and the major pressure drop within the DPI comes from the de-agglomeration of the electro dose in a relation $\Delta P_{de\text{-}agglomeration}/\Delta P_{total}\times 100>50\%$. This can be done by optimizing the aerodynamic construction of the mouthpiece and the device member and reducing the overall pressure drop inside the DPI. The mouthpiece should also be aerodynamically optimized to reduce retention of powder and electrically connected by a dissipative material to the user to eliminate electrical fields that will increase the retention in the mouthpiece.

If the DPI is set for an airflow between 40 and 60 liters/minute the pressure drop could be lower than if the inhalation airflow set for a deep lung delivery with 20 to 40 liters/minute and having the same effect regarding electro-dose de-agglomeration during the dose-delivery time, time (s) or time(a).

After the setting of the inhalation pressure and flow at step 220 follows adjustment and setting of the dose delivery time in step 230 as this is of great importance for deciding delivery to the local lung or the deep lung. The dose delivery time of step 230 should be adjusted to take advantage of the power curve in an inhalation and make use of the highest effect levels and cut off the beginning and end where much less de-agglomeration of the electro-dose will take place. In area I and II in FIG. 6 the de-agglomeration of the electro-dose will have the best possibility to meat a specification set for an EDPI.

To have a deep lung delivery is recommended that the inhalation airflow should be between 20 and 40 liters per minute not to have to high flows when the amount of impaction in the upper airways is a function of speed and having a dependency according to the amount of impaction as a function of inhalation airflow and the square of the particle size. An ideal design specification for a deep lung setting of the DPI is a flow 20 to 40 liters per minute and a pressure drop between 1 and 2 kPa not to have to much constrain on the airways making them smaller and by this increasing the velocity of the air in the airways.

Figure 8:
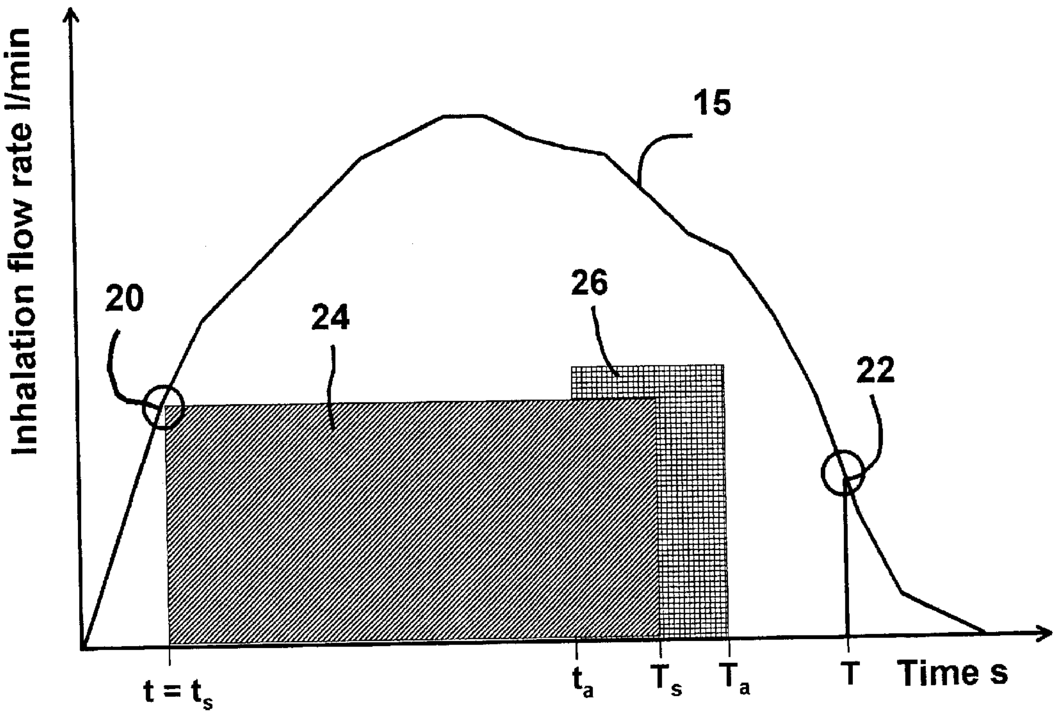
FIG. 8 illustrates the active time and the activation and closing for a deep lung setting and a local lung setting of the DPI with respect to the inhalation flow rate in liters/minute and the time in seconds.

Looking at FIG. 8, a normal inhalation 15 is described with an activation of the DPI with the inhalation flow rate 20 corresponding to an activation pressure and showing a deep lung setting 24 of the DPI compared with a setting 26 for local lung. Both the settings for deep lung and local lung do have the same closing pressure 22. The dose delivery time in step 230 is then set as $t_s$ to $T_s$ for a deep lung setting and from $t_a$ to $T_a$ for a local lung setting of the DPI with an activation pressure setting at t and a closing pressure at T, where the total dosing time for the deep lung setting is time(s)=$T_s$−$t_s$ and the time for local lung setting is time(a)=$T_a$−$t_a$ inside the total activation time for the DPI time=T−t.

Figure 9:
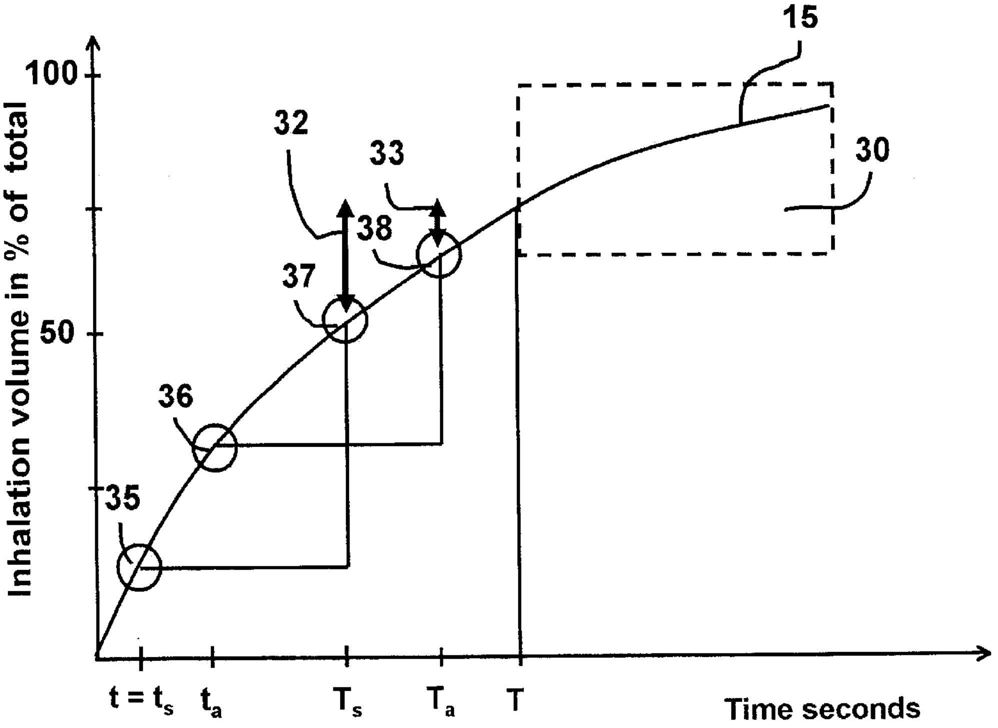
FIG. 9 illustrates the inhalation volume in % of the total inhalation with respect to activation and closing for a deep lung or a local lung setting together with a safety margin of the DPI.

When setting the dose delivery time at step 230 consideration must be made regarding the total a mount of electro-powder that is going to be inhaled not to achieve too a high concentration of powder and ensure a distribution of the powder over the active time. Distributing the electro-dose de-agglomeration over the whole inhalation period is very favorable as this results in that as much as possible of the energy in the inhalation is utilized for de-agglomeration of the electro-dose. An aspect for the dose delivery time in step 230 is also a consideration of the depth of the delivery of the electro-dose into the lung and the amount of air needed for this transport down to the deep lung or the local lung. For local lung delivery normally 0.5 to 2 liters of air is needed but for deep lung delivery 2 to 3 liters is necessary due to the size of the lung and the air volume within the airways. A ideal design specification for the dose delivery time step 230 is for a deep lung delivery from t to t+1.5 seconds, and for a local lung delivery setting from t+1 to t+1.75 seconds, but possible to adjust within the total activation time t to T for the DPI if necessary to ensure an optimized result. Looking at FIG. 9 showing the total inhalation volume 15 of air it is shown that the total inhalation time should not be more than corresponding to 75% of the user's total inhalation volume 15. Area 33 in FIG. 9 illustrates the amount of air volume necessary to transport powder from the inhaler to the local lung and the volume of air in area 32 illustrates the necessary air volume needed to transport powder from the DPI to the deep lung. The activation of the DPI if set for deep lung delivery is at 35 and ending at 37 giving a total dose delivery time as time(s)=$T_s$−$t_s$. For a local lung setting of the DPI the DPI is activated for dose delivery at 36 and ending at 38 giving a total dose delivery time as time(a)=$T_a$−$t_a$. Area 30 represents the variation within the population and serves as a safety margin to always have a setting of the DPI total time shorter than a user's inhalation time DPI time=T−t where also DPI time is less than the time for a user's inhalation.

Having set the dose delivery time at step 230 a next adjustment for the DPI is to set the closing pressure in step 240. The closing pressure at step 240 secures and closes the DPI and is normally set to the same value as the activation pressure at step 210 or lower.

The physical adjustment of the DPI is now set and the DPI is ready for an analysis 1 at step 120 to determine if the prepared DPI meets the specification for an approved DPI at step 130.

If the prepared DPI meets the specification set the process is transferred to step 140 for a prepared DPI. If the specification set is not met the process is transferred back via a step 135 to step 110 for preparation of the DPI by further adjustments.

The DPI prepared at step 140 is set for further tests together with an electro-dose in step 150 and for further tests in step 160 and a second analysis 2 in step 170 to determine if the prepared DPI at step 140 together with the electro-dose at step 150 meets specification set for an EDPI approval at step 190.

The prepared DPI at step 140 is loaded with a metered electro-dose at step 150 and tested in step 160 according to USP. The prepared DPI is further taken into the second analysis 2 at step 170 measuring inhalation pressure and flow in step 220 together with dose delivery time in step 230 and dose de-agglomeration in step 430.

In optimizing the properties of a DPI, de-agglomeration of electro-powder and electro-dose is very important. The de-agglomeration of electro-powder to prepare an electro-dose is defined as de-agglomeration #1 and de-agglomeration of electro-dose by inhalation is defined as de-agglomeration #2.

De-agglomeration #2 is measured at two different airflow values, whereby the first airflow Q is according to USP and the second airflow $Q_{1\ kPa}$ is at a pressure drop over the inhaler device of 1 kPa. The two different airflow values determine if an increase in inhalation energy has a major effect on the de-agglomeration #2. It is important to minimize the effect of the inhalation energy by adjusting the de-agglomeration #2, the dosing properties and de-agglomeration # 1 to meet the EDPI specification.

De-agglomeration #2 is measured using the prepared DPI of step 140.

The de-agglomeration is then calculated using the electro-powder particle size specification as input material and the High Pressure Liquid Chromatography HPLC analysis regarding particle size distribution after a standard sucking off powder from the device member as the output result. The de-agglomeration of the electro-dose is then calculated as percent of de-agglomerated electro-dose at 3 μm, DD3 μm, and 5 μm, DD5 μm, compared to the amount of powder less than 3 μm and 5 μm in the original electro-powder.

FIGS. 17 and 18 present calculations of de-agglomeration at 3 μm and 5 μm, respectively, in a graphical representation marking the areas under the particle size distribution curves for the initial and resulting distributions respectively. The curves plotted with dots representing initial electro-powder size distribution and the curves plotted with squares representing resulting size distribution from the mouthpiece.

FIG. 17 describes how the de-agglomeration at 3 μm is calculated using the initially input electro-powder under 3 μm represented by the hatched area as a base. The amount of de-agglomerated powder from the electro-dose is then represented by the dark area under the curve showing resulting powder. By dividing the calculated value of the surface of the second area with the calculated value of the surface of the first area and multiplying by a factor 100 the de-agglomerated amount below 3 μm is obtained in percent referred to as DD3 μm.

FIG. 18 describes how the de-agglomeration at 5 μm is calculated using the initially input electro-powder below 5 μm represented by the hatched area as a base. The dark area under the curve showing resulting powder represents the amount of de-agglomerated electro-powder from the electro-dose. By dividing the calculated value of the surface of the second area with the calculated value of the surface of the first area in FIG. 18 and multiplying by a factor 100 the de-agglomerated amount below 5 μm is obtained in percent referred to as DD5 μm.

The prepared DPI at step 140 will meet the specification for an EDPI if the electro-dose de-agglomeration analysis at step 430 shows a de-agglomeration difference measured according to USP compared with the de-agglomeration at a flow representing a pressure drop over the inhaler device reduced to 1 kPa (1−(de-agglomeration($Q_{1\ kpa}$)/de-agglomeration(Q))×100)<50% and preferably less than 25% and most preferably less than 10% referred to as ΔDD3 μm and ΔDD5 μm for deep lung and local lung DPI analysis of de-agglomeration difference.

Figure 19:
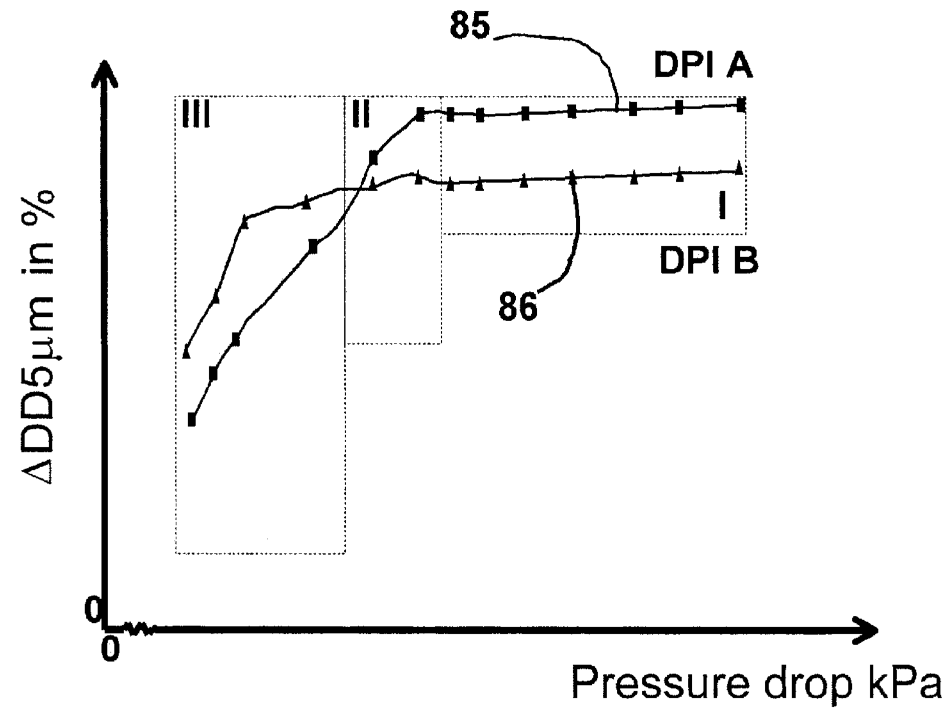
FIG. 19 is a graph showing the amount of de-agglomeration at 5 $\mu$m (DD5 $\mu$m) at different pressure drops measured as kPa over the DPI.

This correlation is also best understood by looking at FIG. 19 showing the de-agglomeration 5 μm in % for DPI A 85 and for DPI B 86 where DPI A shows a higher degree of de-agglomeration at higher pressure drops over the DPI properly because that the inhaler DPI A is having higher flow and therefore also a bigger power for de-agglomeration of the electro-dose. The velocity in DPI A is dropping quicker and at medium to low pressure drops the DPI A 85 is showing less de-agglomeration than the DPI B 86.

The dose mass step 440 is measured to determine the uniformity of dose according to USP by chemical analyzes, e.g. a HPLC SpectraSYSTEM with a UV 6000 detector or any other suitable detector. A second option and also most preferable is to determine the powder mass using an Andersen Impactor and analyze both the aerodynamic particle size distribution and the total mass using for instance the HPLC SpectraSYSTEM in accordance with USP.

Figure 20:
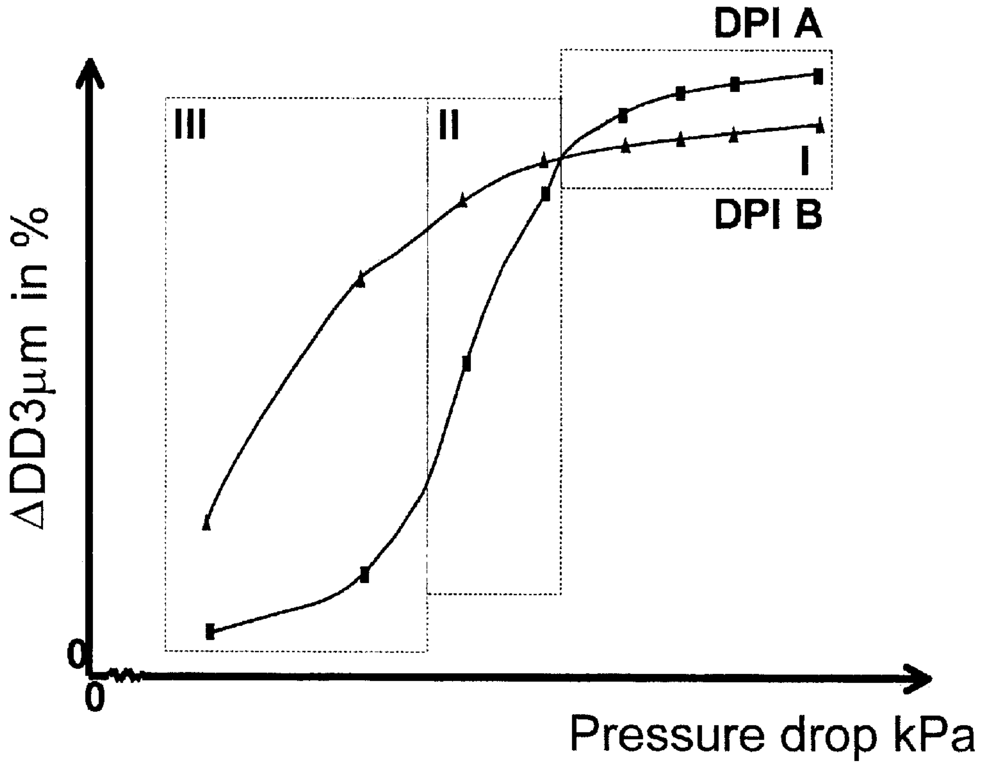
FIG. 20 is a graph showing the amount of de-agglomeration at 3 $\mu$m (DD3 $\mu$m) at different pressure drops measured as kPa over the DPI.

The dose retention at step 450 is defined as the unwanted amount of remaining electro-powder in the prepared DPI of step 140 after an inhalation or test at step 160 has been performed. FIG. 20 shows how the amount of retention 88 in % is changed when the pressure drop over the DPI is changed. The setting of the DPI to have and optimal prepared DPI at step 140 is important to minimize the retention and improve uniformity of dose. A low pressure drop I will have a higher retention due to less effect in the inhalation and a to high pressure drop III will show more turbulence and by this more electro-powder will stick to the mouthpiece.

A data analysis in step 460 is performed and resulting in graphs according to FIGS. 6 to 9, FIGS. 11 to 12, and FIGS. 16 to 20. All graphs are analyzed to determine if the prepared DPI meets the specification set for an EDPI or is subject to optimization by going back via step 182 to preparation of DPI or the electro-dose needs to be optimized by going back via step 184 to electro-dose step 150.

Figure 10:
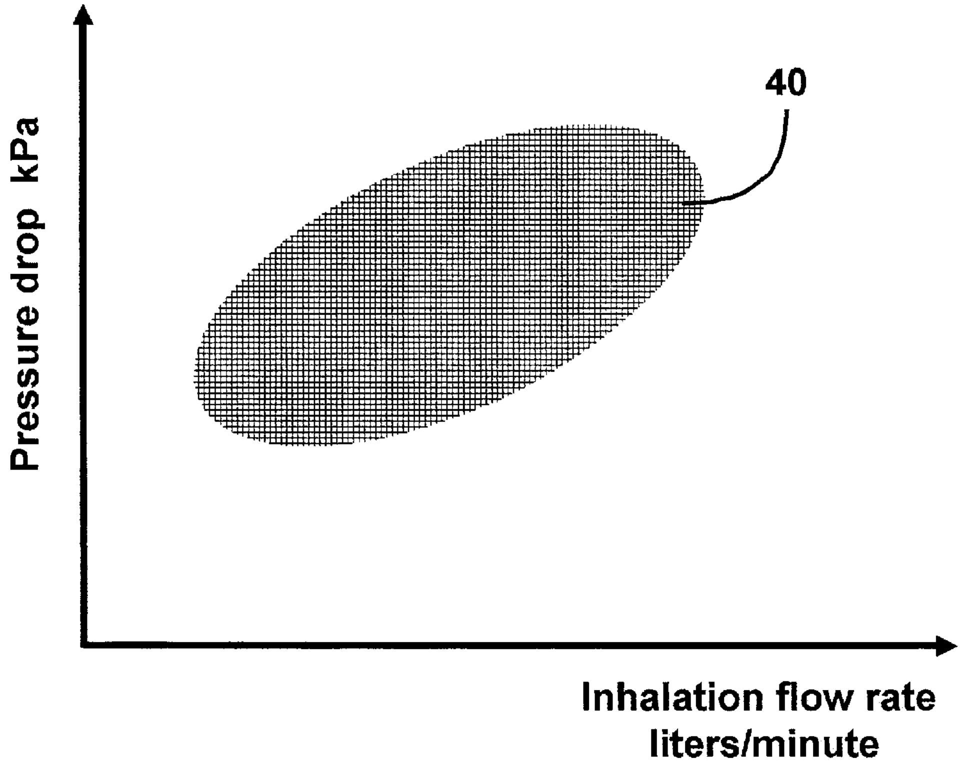
FIG. 10 illustrates the comfort area for an inhalation through a DPI as a mean over a population measured as inhalation flow rate in liters per minute versus pressure drop in kPa.

FIG. 10 shows how different users experience the inhalation pressure versus the inhalation flow rate and the comfort area 40 represents the area where the users have a comfortable inhalation through and DPI normally the pressure drop must be below 4 kPa and the flow rate between 20 and 80 liters/minute.

Figure 11:
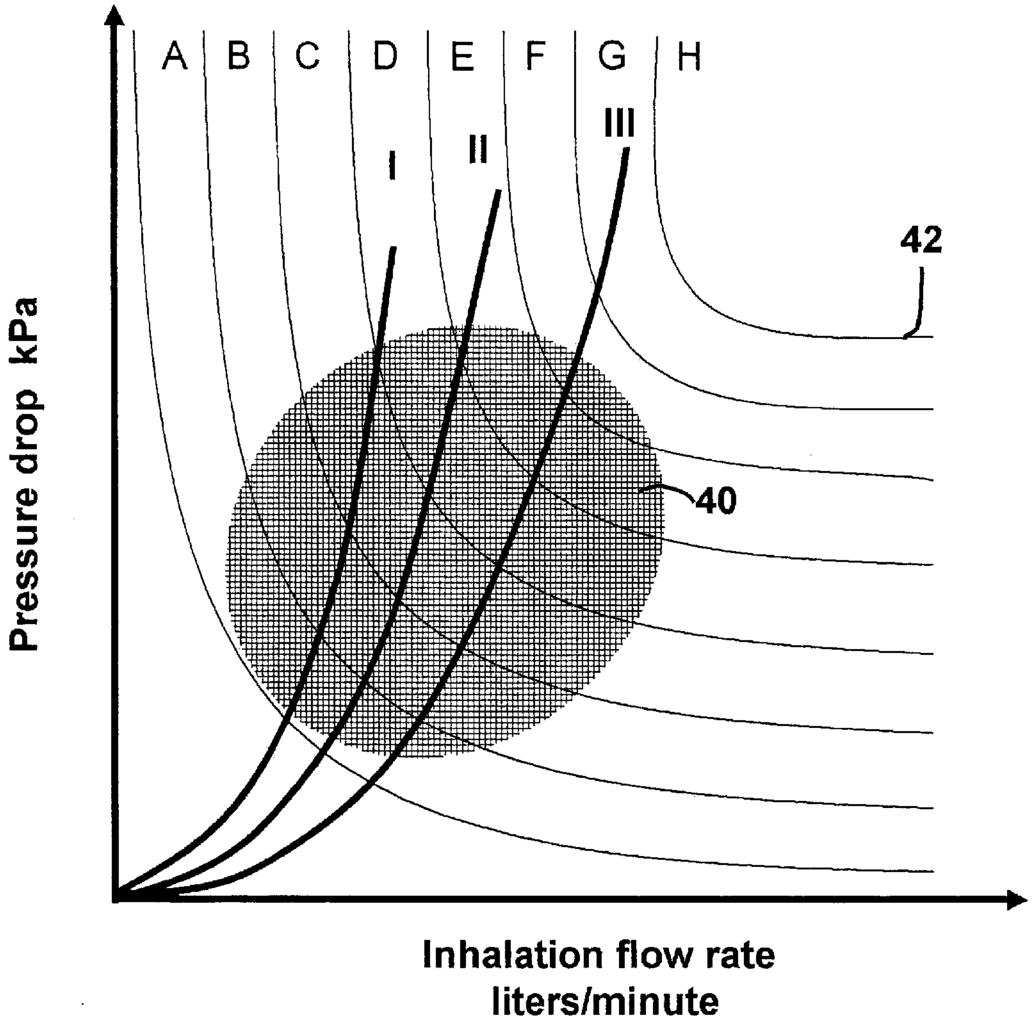
FIG. 11 illustrates the power levels compared with the comfort area of inhalation in accordance with FIG. 10.

FIG. 11 shows the comfort area 40 inside a graph showing tests with three (3) different DPI settings I, II, III and effect levels 42 A to H. The power levels are between 0.1 to 6 watts and inhalation flow rates 20 to 80 liters/minute and pressure drop over the DPI between 0.5 and 4 kPa. The graph will show how to best prepare the DPI with respect to inhalation comfort of the user.

Figure 12:
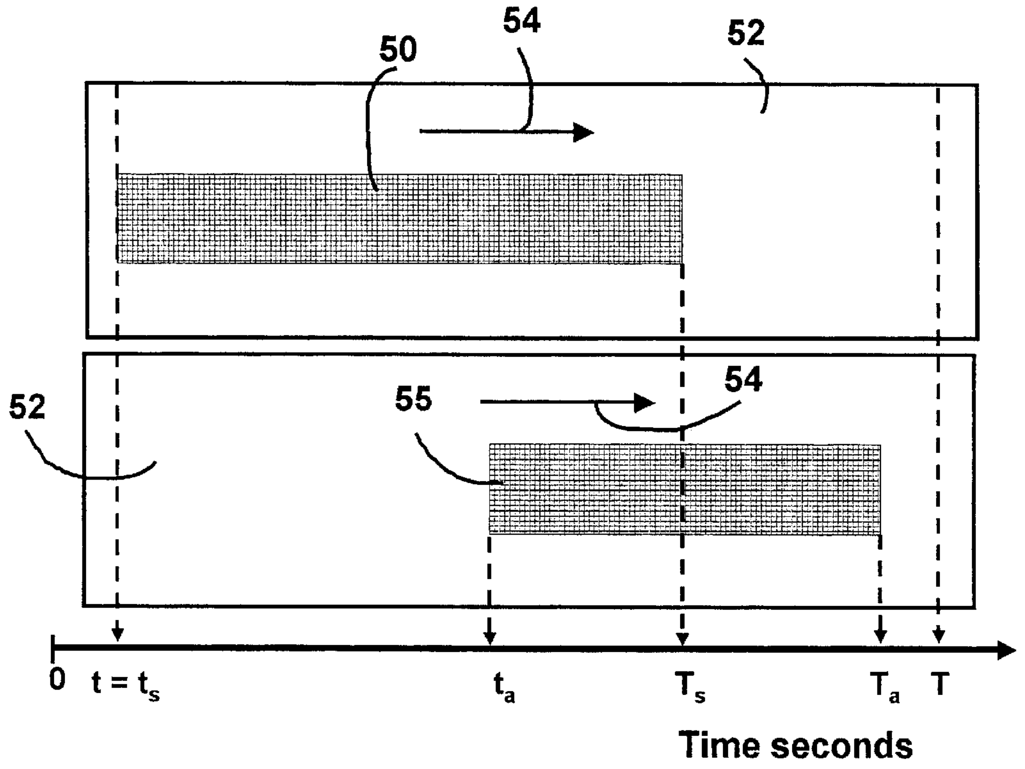
FIG. 12 illustrates two device members with layouts for systemic delivery or local lung delivery of the electro-dose with respect to time in seconds.

FIG. 12 shows a layout of two (2) different device members of electro-doses. Electro-dose 50 represents a deep lung setting between $t_s$ and $T_s$ with a de-agglomeration direction 54. Electro-dose 55 represents a local lung setting between $t_a$ and $T_a$ also with a direction of de-agglomeration 54 and where T represents the total activation time of the DPI. The dose delivery time can be adjusted relative to a time for a user's full inspiration by adjusting a length of the electro-dose 50/55.

The device member 52 can be made out of isolative, dissipative or conductive polymers characterized in that electro-conductive material used for the device member is obtained from materials such as silver powder, platinum powder, gold powder, stainless steel powder, antimony-doped tin oxide, antimony-doped silica oxide, or is an X-doped silica where X is an adamantine semiconductor, e.g., Ge, Zno, GaSb or an octahedral semiconductor, e.g. SnSE, AgSbSe2, InSb or carbon or any other electro-conductive material approved by FDA and possible to incorporate into plastics. And also that the conductive material and the plastic material for a dissipative or conductive combination of the device member has a specification presenting a surface resistance of $10^3$–$10^{12}$Ω, and a volume resistivity of $10^3$–$10^{12}$ ohm·m.

Figure 14:
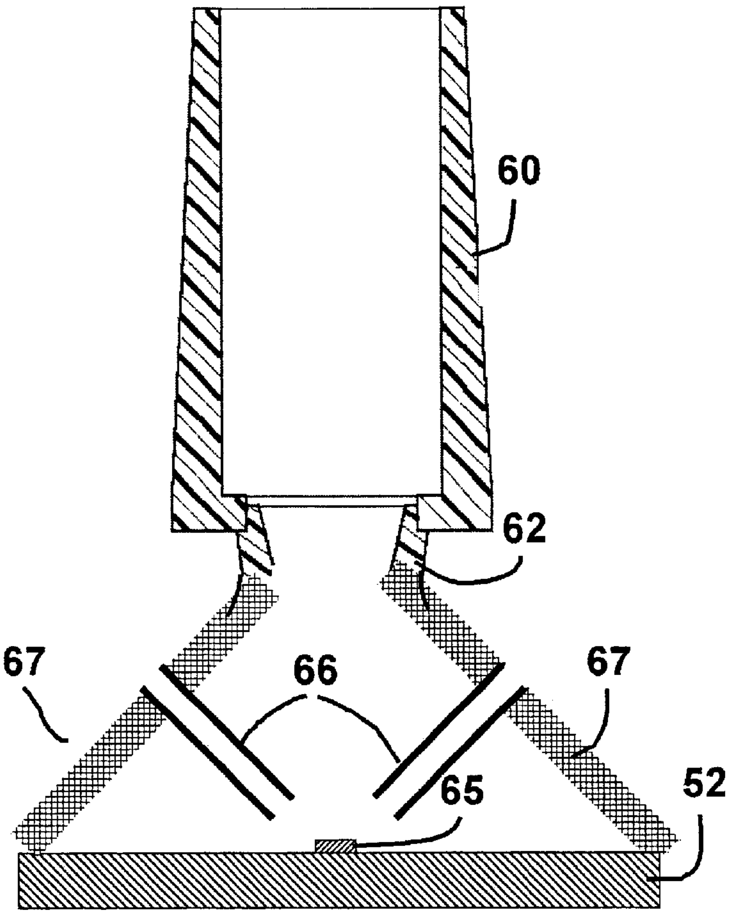
FIG. 14 illustrates a second example of an aerodynamically optimized mouthpiece together with an electro-dose on a device member.

FIG. 14 shows an illustrative example of a mouthpiece 60 and a diffuser 62 where the electro-dose 65 is blown of the device member 52 by high velocity air coming through tubes 66. The blown off powder from electro-dose is cleared from the active walls 67 by having 10 to 75% of the inhalation air coming thorough the active walls 67.

Figure 15:
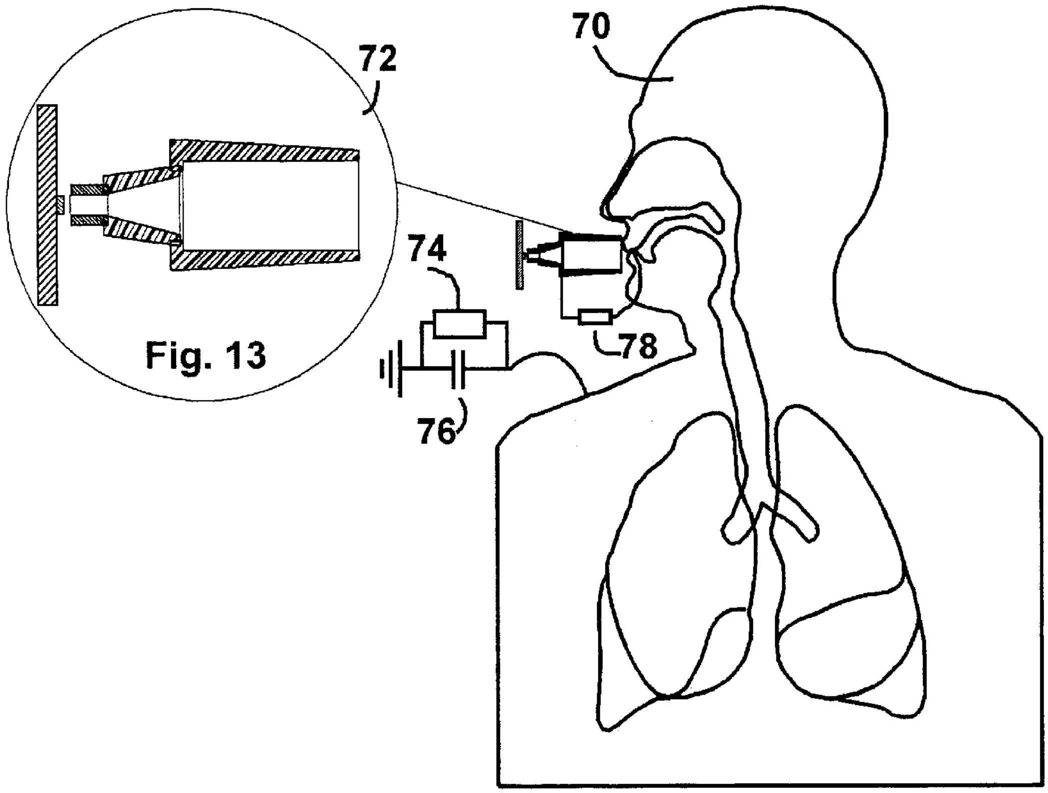
FIG. 15 illustrates a connection between a user and the DPI through a dissipative or conductive mouthpiece.
Figure 16:
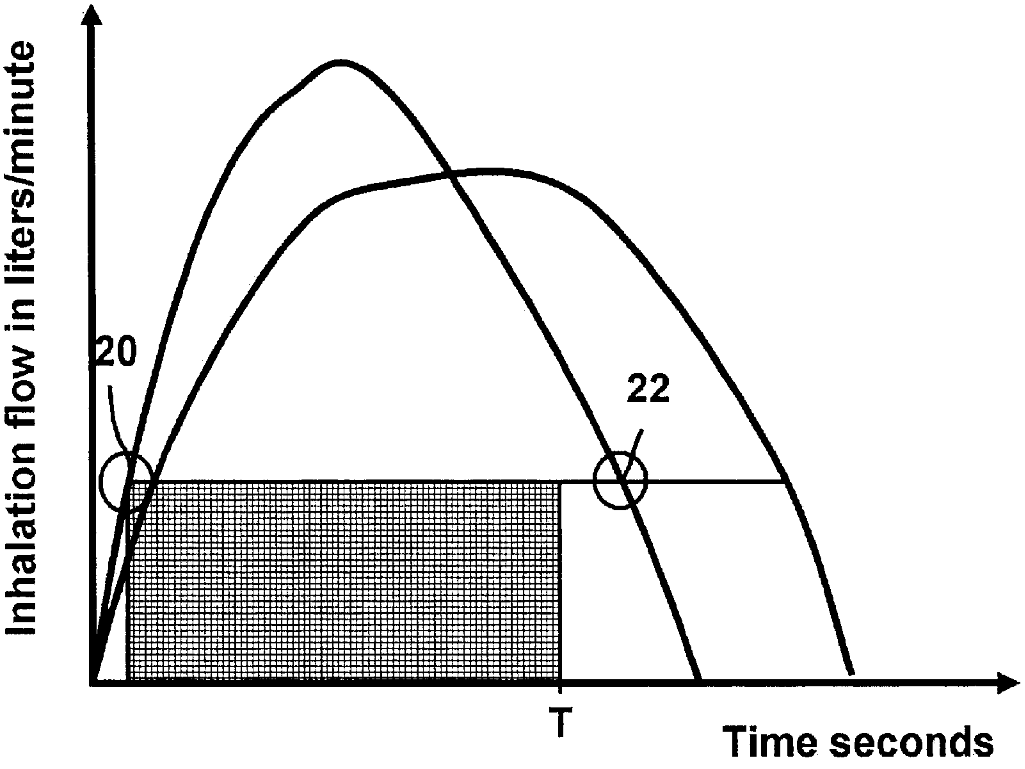
FIG. 16 is graph representing two different inhalations together with activation and closing of the DPI with respect to inhalation airflow in liters/minute and time in seconds.

FIG. 15 shows in an illustrative example a connection between the EDPI 72 having a conductive or dissipative mouthpiece and where the connection between a user 70 and an EDPI 72 is through the lips with a contact resistance 78. The charge of the user is represented by the capacitance 76 and the user 70 charge build up is drained thorough a resistor 74. By having a dissipative material in contact with the lips of the user, the EDPI and the user 70 will have the same potential and no electrical fields disturbing the electro-powder will be present.

The description above will be better understood when looking at two examples whereby exampel is for a local lung deposition and example 2 is for a systemic delivery of powder.

EXAMPLE 1

Two different settings of the intended DPI at step 100 suited for an electro-dose in step 150 using Terbutaline sulphate (TBS) 100 $\mu$g for local lung delivery are prepared according to the following specification.

The specification for the DPI has been determined by looking at FIG. 6 achieved from preparing the electro-dose and analyzing of the electro-dose showing the need of power in watts to de-agglomerate the electro-dose of TBS.

The general setting for a local lung delivery is to have 60 liters/minute inhalation flow and from this it is possible from FIG. 6 to calculate a pressure drop over the DPI that will give a de-agglomeration within set specification for an EDPI of TBS.

Figure 13:
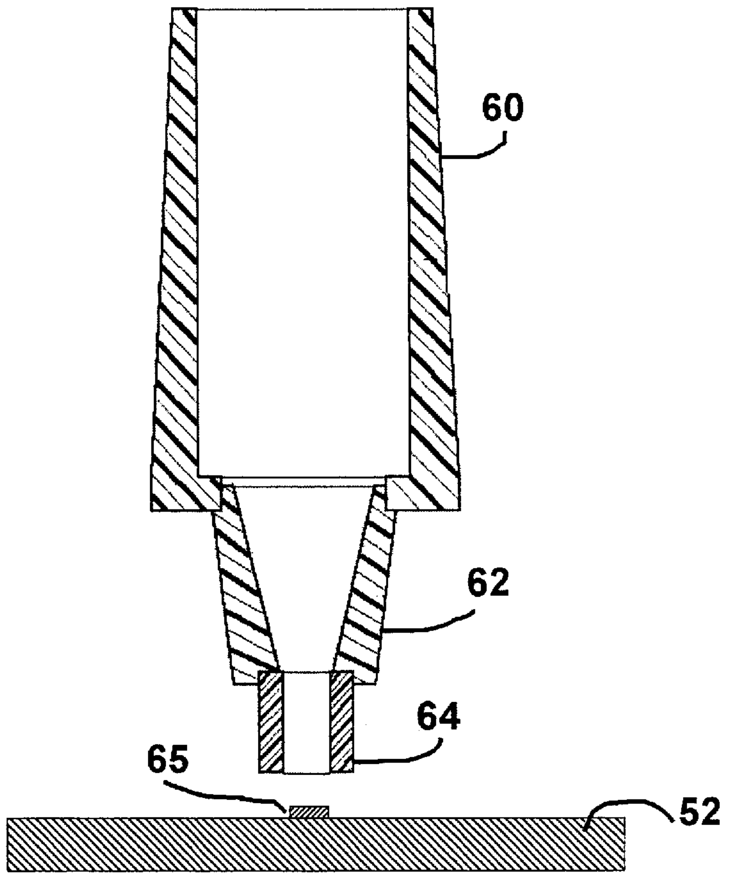
FIG. 13 illustrates a first example of an aerodynamically optimized mouth-piece together with an electro-dose on a device member.

The above settings are possible to achieve by adjusting different measurements inside the DPI. FIG. 13 is showing an illustrative example of a mouthpiece with an electro-dose situated right under the opening. In this construction it is possible to change the distance between the device member 52 and the nozzle 64 to introduce a higher resistance or alter the size of the mouthpiece 60 or reduce the middle section 62 to have different aerodynamic properties.

FIG. 14 shows a second illustrative embodiment where different settings of the DPI are possible by changing nozzles 66 or distances or mouthpiece 60 together with the middle section 62.

The aim of the settings for the DPI is to obtain an inhaler that will be as little as possible dependent on the inhalation path of the user and will give the best de-agglomeration of the electro-dose of TBS measured as DD5 $\mu$m inside the comfort region 40 according to FIGS. 10 and 11.

| | | |
|---|---|---|
| DPI A | | |
| Inhalation flow | 60 | liters/minute |
| Inhalation pressure | 2 | kPa |
| Activation pressure | 1.5 | kPa |
| Dose delivery time $t_a$ | 1 | s |

-continued

| | | |
|---|---|---|
| Dose delivery time $T_a$ | 1.8 | s |
| Activation time DPI T - t | 3.0 | s |
| Closing pressure | 1.5 | kPa |
| Electrical connected | | yes |
| DPI B | | |
| Inhalation flow | 60 | liters/minute |
| Inhalation pressure | 3 | kPa |
| Activation pressure | 1.5 | kPa |
| Dose delivery time $t_a$ | 1 | s |
| Dose delivery time $T_a$ | 1.8 | s |
| Activation time DPI T - t | 3.0 | s |
| Closing pressure | 1.5 | kPa |
| Electrical connected | | yes |

These parameters are identified as the most suitable for a TBS electro-dose after analyzing FIG. 6 where the most suitable inhalation power in watts is determined for the TBS electro-dose at step 150. The activation pressure step 210 is set with respect to FIG. 7 where the optimum effect in the inhalation is in region I and in region I the inhalation power is also at a maximum and the de-agglomeration of the electro-dose will be at an optimum. The time when the activation pressure is reached is at t=$t_s$ according to FIG. 8 and at activation flow rate 20.

After the preparation of the DPI at step 110 the respective inhaler is set to analysis 1 step 120 to determine if the settings are according to intended specification. All measurements are made according to USP and a set-up according to FIG. 1 is used to measure the uniformity of dose and the dose de-agglomeration DD5 $\mu$m.

All pressures are measured in the same way as the pressure drop over the DPI 8 as described in USP together using a chronograph to measure the times during the DPI activation time in step 250.

Results from Analysis 1 in step 120

| | | | |
|---|---|---|---|
| DPI A | | | |
| Inhalation flow | 60 | liters/minute | OK |
| Inhalation pressure | 2.1 | kPa | OK |
| Activation pressure | 1.4 | kPa | OK |
| Dose delivery time ta | 0.9 | s | OK |
| Dose delivery time Ta | 1.6 | s | OK |
| Activation time DPI T - t | 2.8 | s | OK |
| Closing pressure | 1.5 | kPa | OK |
| Electrical connected | yes | | OK |
| DPI B | | | |
| Inhalation flow | 60 | liters/minute | OK |
| Inhalation pressure | 3.2 | kPa | OK |
| Activation pressure | 1.4 | kPa | OK |
| Dose delivery time ta | 1 | s | OK |
| Dose delivery time Ta | 1.8 | s | OK |
| Activation time DPI T - t | 2.9 | s | OK |
| Closing pressure | 1.5 | kPa | OK |
| Electrical connected | yes | | OK |

Analysis 1 at step 120 shows an approved result and both DPI A and DPI B is approved for further test and meet in step 140 the requirements for the prepared DPI.

An electro-dose of step 150 with TBS is now introduced and is inserted into the DPI for further tests at step 160.

A set of tests at different pressures according to FIG. 19 are defined and performed where the de-agglomeration is measured and the point where the de-agglomeration is changing drastically as in transition region II and region III with the pressure identified. Analysis is performed in accordance with USP and in a set up according to FIG. 1 and measured using a HPLC.

As can be seen in FIG. 19 the DPI A shows a worse behavior in region II compared with DPI B. If possible with respect to user comfort region 40 according to FIG. 10 and behavior inside the comfort area according to FIG. 11 the DPI B presents a more safe setting but the DPI A has a higher performance inside region I.

| Pressure drop | De-agglomeration DD5 μm % | | Retention % | |
|---|---|---|---|---|
| kPa | DPI A | DPI B | DPI A | DPI B |
| 0.5 | 17 | 35 | 6.5 | 6 |
| 1 | 31 | 54 | 6 | 5 |
| 1.5 | 40 | 57 | 5 | 5 |
| 2 | 55 | 66 | 5 | 4 |
| 2.5 | 68 | 68 | 4 | 4 |
| 3 | 76 | 68 | 5 | 4 |
| 3.5 | 78 | 69 | 7 | 5 |
| 4 | 82 | 70 | 7 | 6 |

Figure 21:
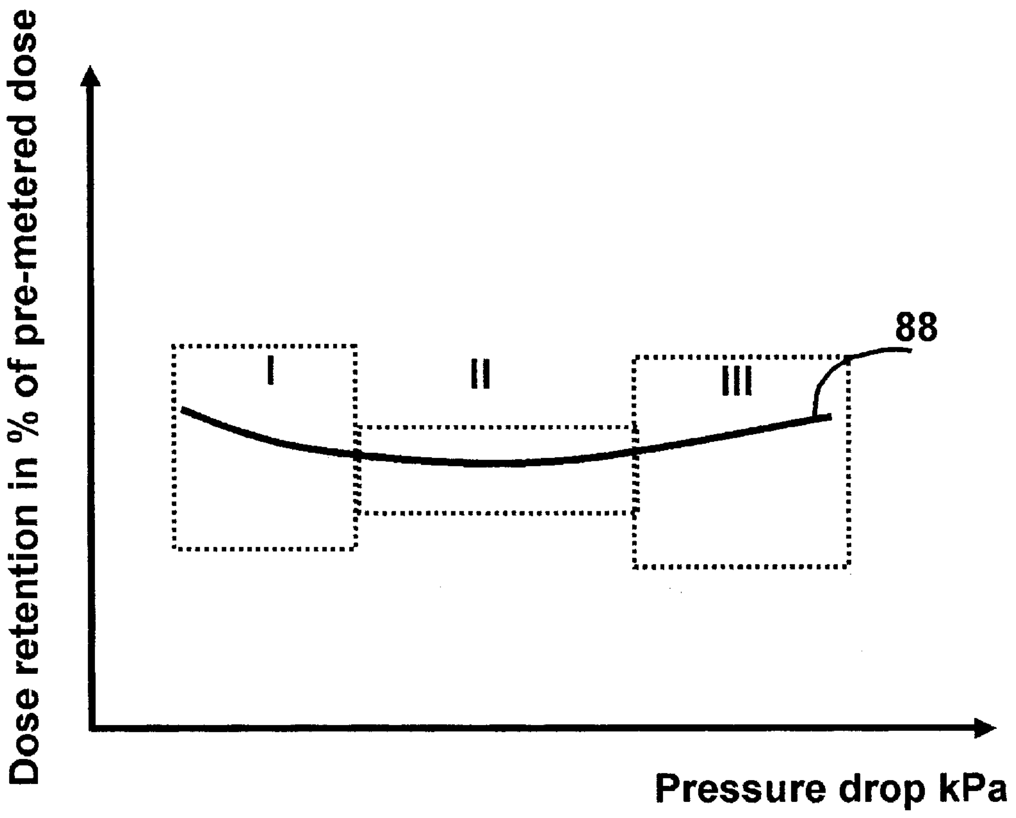
FIG. 21 is a graph showing the amount retention in the DPI at different pressure drops over the DPI measured as % of the pre-metered dose.

Regarding dose retention 88 FIG. 21 shows the need to optimize the DPI to be used into region II.

A report for determining approved Y/N of step 180 is prepared to present the results of analysis 2.

Results from Analysis 2

| | | | |
|---|---|---|---|
| DPI A | | | |
| Inhalation flow | 60 | liters/minute | OK |
| Inhalation pressure | 2.1 | kPa | OK |
| Activation pressure | 1.4 | kPa | OK |
| Dose delivery time ta | 0.9 | s | OK |
| Dose delivery time Ta | 1.6 | s | OK |
| Activation time DPI T - t | 2.8 | s | OK |
| Closing pressure | 1.5 | kPa | OK |
| Electrical connected | yes | | OK |
| DD5 μm | 55 | % | OK |
| Retention | 5 | % | OK |
| DPI B | | | |
| Inhalation flow | 60 | liters/minute | OK |
| Inhalation pressure | 3.2 | kPa | OK |
| Activation pressure | 1.4 | kPa | OK |
| Dose delivery time ta | 1 | s | OK |
| Dose delivery time Ta | 1.8 | s | OK |
| Activation time DPI T - t | 2.9 | s | OK |
| Closing pressure | 1.5 | kPa | OK |
| Electrical connected | yes | | OK |
| DD5 μm | 75 | % | OK |
| Retention | 5 | % | OK |

To verify if the DPI conforms to the specification of an EDPI the following calculations must be made.

| | EDPI | DPI A | DPI B |
|---|---|---|---|
| DD5 μm | >25% | 55% | 68% |
| Dose | 2 μg–2 mg | 100 μg | 100 μg |
| ΔDD5 μm | <50% | 62% | 23% |
| Uniformity of dose | according to USP | Approved | Approved |

DPI B shows an approved result in step 180 for the optimization and is suitable for local lung deposition of TBS as an EDPI loaded with an electro-dose of TBS. DPI A shows a high ΔDD5 μm of 62% and is not approved as an EDPI for TBS as this indicates that the DPI A is not independent of the user's inhalation pattern. DPI A is considered for further optimization at the DPI step 182 and/or an optimization of the electro-dose of TBS at step 184.

EXAMPLE 2

Two different settings of the intended DPI at step 100 suited for an electro-dose in step 150 using Insulin (INS) 800 μg for local lung delivery are prepared according to the following specification.

The specification for the DPI has been determined by looking at FIG. 6 achieved from preparing the electro-dose and analyzing of the electro-dose showing the need of power in watts to de-agglomerate the electro-dose of INS.

The general setting for a local lung delivery is to have 40 liters/minute inhalation flow and from this it is possible from FIG. 6 to calculate a pressure drop over the DPI that will give a de-agglomeration within set specification for an EDPI of INS.

| | | |
|---|---|---|
| DPI A | | |
| Inhalation flow | 40 | liters/minute |
| Inhalation pressure | 1.5 | kPa |
| Activation pressure | 1.0 | kPa |
| Dose delivery time ts | 0.5 | s |
| Dose delivery time Ts | 2.0 | s |
| Activation time DPI T - t | 3.0 | s |
| Closing pressure | 1.0 | kPa |
| Electrical connected | yes | |
| DPI B | | |
| Inhalation flow | 40 | liters/minute |
| Inhalation pressure | 2.5 | kPa |
| Activation pressure | 1.0 | kPa |
| Dose delivery time $t_s$ | 0.5 | s |
| Dose delivery time $T_s$ | 2.0 | s |
| Activation time DPI T - t | 3.0 | s |
| Closing pressure | 1.0 | kPa |
| Electrical connected | yes | |

The aim of the settings for the DPI is to have a inhaler that is as little as possible dependent on the inhalation path of the user and gives the best de-agglomeration of the electro-dose of INS measured as DD3 μm inside the comfort region 40 according to FIGS. 10 and 11.

These parameters are identified as the most suitable for an INS electro-dose after analyzing FIG. 6 where the most suitable inhalation power in watts is determined for the INS electro-dose in step 150. The activation pressure step 210 is set with respect to FIG. 7 where the optimum effect in the inhalation is in region I and in region I the inhalation power is also at a maximum and the de-agglomeration of the electro-dose will be optimal. The time when the activation pressure is reached is at $t=t_s$ according to FIG. 8 and at activation flow rate 20.

After the preparation of the DPI at step 110 the respective inhaler is set to analysis 1 step 120 to determine if the settings are in accordance with the intended specification.

All measurement is made according to USP and a set-up according to FIG. 1 is used to measure the uniformity of dose and the dose de-agglomeration DD3 μm.

Results from Analysis Step 120

| | | | |
|---|---|---|---|
| DPI A | | | |
| Inhalation flow | 40 | liters/minute | OK |
| Inhalation pressure | 1.6 | kPa | OK |
| Activation pressure | 0.5 | kPa | OK |
| Dose delivery time ts | 0.5 | s | OK |
| Dose delivery time Ts | 2.1 | s | OK |
| Activation time DPI T - t | 3.1 | s | OK |
| Closing pressure | 1.0 | kPa | OK |
| Electrical connected | yes | | OK |
| DPI B | | | |
| Inhalation flow | 40 | liters/minute | OK |
| Inhalation pressure | 2.6 | kPa | OK |
| Activation pressure | 0.5 | kPa | OK |
| Dose delivery time ts | 0.5 | s | OK |
| Dose delivery time Ts | 2.1 | s | OK |
| Activation time DPI T - t | 3.1 | s | OK |
| Closing pressure | 0.7 | kPa | OK |
| Electrical connected | yes | | OK |

All pressures are measured in the same way as the pressure drop over the DPI 8 described in the USP together with a chronograph to measure the times during the activation time DPI step 250.

Analysis 1 in step 120 shows approved results and both DPI A and DPI B are approved for further test and meet at step 140 the requirements for a prepared DPI.

An electro-dose step 150 of INS is now introduced and inserted into the respective DPI for further tests at step 160.

A set of tests at different pressures according to FIG. 20 are defined and performed where the de-agglomeration is measured and the point where the de-agglomeration is changing drastically as in transition region II and region III with the pressure identified. Analyzes are performed in accordance with USP and in a set up according to FIG. 1 and measured using a HPLC.

As can be see in FIG. 20 the DPI A is showing a worse behavior in region II compared with DPI B. If possible with respect to user comfort region 40 according to FIG. 10 and behavior inside the comfort area according to FIG. 11 the DPI B is a more safe setting but the DPI A is having a higher performance inside region I.

Regarding dose retention 88 FIG. 21 shows the need to optimize the DPI to be used into region II.

A for determining approved Y/N step 180 is prepared giving the results of analysis 2.

| Pressure drop | De-agglomeration DD3 μm % | | Retention % | |
|---|---|---|---|---|
| kPa | DPI A | DPI B | DPI A | DPI B |
| 0.5 | 22 | 27 | 5 | 5 |
| 1 | 57 | 52 | 4 | 5 |
| 1.5 | 59 | 57 | 3 | 4 |
| 2 | 62 | 59 | 3 | 3 |
| 2.5 | 63 | 60 | 4 | 3 |
| 3 | 64 | 61 | 5 | 5 |
| 3.5 | 66 | 62 | 6 | 5 |
| 4 | 67 | 62 | 7 | 6 |

-continued

| | | | |
|---|---|---|---|
| DPI A | | | |
| Inhalation flow | 40 | liters/minute | OK |
| Inhalation pressure | 1.6 | kPa | OK |
| Activation pressure | 0.5 | kPa | OK |
| Dose delivery time ta | 0.5 | s | OK |
| Dose delivery time Ta | 2.1 | s | OK |
| Activation time DPI T - t | 3.1 | s | OK |
| Closing pressure | 1.0 | kPa | OK |
| Electrical connected | yes | | OK |
| DD3 μm | 59 | % | OK |
| Retention | 3 | % | OK |
| DPI B | | | |
| Inhalation flow | 40 | liters/minute | OK |
| Inhalation pressure | 2.6 | kPa | OK |
| Activation pressure | 0.5 | kPa | OK |
| Dose delivery time $t_s$ | 0.5 | s | OK |
| Dose delivery time $T_s$ | 2.1 | s | OK |
| Activation time DPI T - t | 3.1 | s | OK |
| Closing pressure | 0.7 | kPa | OK |
| Electrical connected | yes | | OK |
| DD3 μm | 60 | % | OK |
| Retention | 3 | % | OK |

To verify if the DPI conforms to the specification of an EDPI the following calculations must be made.

| | EDPI | DPI A | DPI B |
|---|---|---|---|
| DD3 μm | >25% | 59% | 60% |
| Dose | 2 μg–2 mg | 800 μg | 800 μg |
| ΔDD3 μm | <50% | 15% | 16% |
| Uniformity of dose | according to USP | Approved | Approved |

Both DPI A and DPI B show approved results and are suitable for systemic delivery of INS 800 μg as EDPI inhalers for INS 800 μg. To determine if DPI A or DPI B is going to be decided for, further tests has to be performed by utilizing both analysis 1 in step 120 and analysis 2 in step 170 together and with users determining what inhalation pressure and flow they prefer to be inside a comfort area step 40. It may also be considered that the de-agglomeration of the powder is to poor and further optimization of the deep lung delivery performance of DPI A and DPI B is be executed together with an optimization of the electro-dose step 150 of INS.

In FIG. 22 is summarized some of the features of an EDPI and which demonstrate the versatility of this kind of dry powder inhaler for administration of a medical drug or the like by means of inhalation dosing of a powder. Particularly the continuous delivered dose during a prolonged time period in combination with a full control of total inhalation time and flow/pressure settings will guarantee a good yield of a used electro-powder.

What is claimed is:

1. A method for optimizing an electrostatically dosed dry powder inhaler (EDPI) for utilization of a prepared pre-metered electro-dose consisting of an electro-powder, comprising the steps of arranging a measurement set-up for measurement of parameters affecting a systemic delivery or local lung delivery of a pre-metered electro-dose from a dry powder inhaler (DPI) including analysis of dose de-agglomeration, particle size distribution as well as uniformity of dose together with pressures times and flows according to USP;

adjusting said DPI for a systemic or a local lung setting with respect to an activation pressure and a closing pressure having a DPI with a 20 to 60 liters/minute inhalation air flow for a systemic delivery setting and 20 to 80 liters/minute for a local lung setting;

adjusting a de-agglomeration power between 0.1 and 6 watts to be used in said DPI by optimizing a pressure drop and an inhalation flow rate by changes to a mouthpiece and/or a device member and their relation to each other;

adjusting said activation pressure between 0.5 and 4 kPa and said closing pressure between 0.5 and 4 kPa to eliminate low power at the start and end of the inhalation;

verifying that said DPI meets specifications set regarding the de-agglomeration power and said activation and closing pressures together with timings within an active time of the DPI;

verifying that a de-agglomeration difference, expressed in percent using an expression 100[1− de-agglomeration ($Q_{1\ kpa}$/de-agglomeration(Q)], is not more than 50%, where $Q_{1\ kPa}$ represents a pressure drop over the inhaler device reduced to 1 kPa and Q represents a reference pressure drop;

verifying that a uniformity of dose meets a uniformity standard; and verifying and optimizing a not approved DPI by further adjusting said DPI and/or electro-dose to meet specifications of an EDPI.

2. The method according to claim 1, comprising the further step of using an instrument for a physical particle size measurement in the measurement set up.

3. The method according to claim 1, comprising the further step of pre-defining a dose fine particle fraction of electro-powder particle size to be 3 $\mu$m or less for a systemic delivery dose.

4. The method according to claim 1, comprising the further step of pre-defining a dose fine particle fraction of electro-powder particle size to be 5 $\mu$m or less for a localized lung delivery dose.

5. The method according to claim 1, comprising the further step of optimizing the de-agglomeration difference to be less than 25%.

6. The method according to claim 1, comprising the further step of optimizing the de-agglomeration difference to be less than 10%.

7. The method according to claim 1, comprising the further step of optimizing the uniformity of dose to meet 90 to 110%.

8. The method according to claim 1, comprising the further step of optimizing the uniformity of dose to meet 95 to 105%.

9. The method according to claim 1, comprising the further step of optimizing the dose de-agglomeration (DD3 $\mu$m) for deep lung delivery to be more than 25%.

10. The method according to claim 1, comprising the further step of optimizing the dose de-agglomeration (DD5 $\mu$m) for local lung delivery to be more than 25%.

11. The method according to claim 1, comprising the further step of optimizing the pressure drop over the mouthpiece and the device member compared to a total pressure drop over the inhaler to be greater than 50%.

12. The method according to claim 1, comprising the further step of optimizing a dissipative connection between a user and the DPI to eliminate electrical fields due to potential differences.

13. The method according to claim 1, comprising the further step of adjusting a dose delivery time in relation to a time for a user's full inspiration by adjusting a length of a powder strip on a dosing member used.

14. A process for optimizing an electrostatically dosed dry powder inhaler (EDPI) for utilization of a prepared pre-metered electro-dose consisting of an electro-powder, comprising an arrangement of a measurement set-up for measurement of parameters affecting a systemic delivery or local lung delivery of a pre-metered electro-dose from a dry powder inhaler (DPI) including analysis of dose de-agglomeration, particle size distribution as well as dose-to-dose variation together with pressures times and flows according to USP;

an adjustment of the DPI for a systemic or a local lung setting with respect to an activation pressure and a closing pressure having said DPI with a 20 to 60 liters/minute inhalation air flow for a systemic delivery setting and 20 to 80 liters/minute for a local lung setting;

an adjustment of a de-agglomeration power between 0.1 and 6 watts to be used in said DPI by optimizing a pressure drop and an inhalation flow rate by changes to a mouthpiece and/or a device member and their relation to each other;

an adjustment of the activation pressure between 0.5 and 4 kPa and the closing pressure between 0.5 and 4 kPa to eliminate a low power at the start and end of the inhalation;

a verification that the DPI meets specifications set regarding the de-agglomeration power and the activation and the closing pressures together with timings within an active time of the DPI;

a verification that a de-agglomeration difference, expressed in percent using an expression 100[1−de-agglomeration($Q_{1\ kpa}$/de-agglomeration(Q)], is not more than 50%, where $Q_{1\ kPa}$ represents a pressure drop over the inhaler device reduced to 1 kPa and Q represents a reference pressure drop;

a verification that a uniformity of dose meets a uniformity standard; and a verification and optimization of a not approved DPI by adjustment of said DPI and/or electro-dose to meet specifications of an EDPI.

15. The process according to claim 14, comprising a utilization of an instrument for a physical size measurement in the measurement set up.

16. The process according to claim 14, comprising a pre-definition of a dose fine particle fraction of electro-powder particle size to be 3 $\mu$m or less for a systemic delivery dose.

17. The process according to claim 14, comprising a pre-definition of a dose fine particle fraction of electro-powder particle size to be 5 $\mu$m or less for a localized lung delivery dose.

18. The process according to claim 14, comprising an optimization of the de-agglomeration difference to be less than 25%.

19. The process according to claim 14, comprising an optimization of the de-agglomeration difference to be less than 10%.

20. The process according to claim 14, comprising an optimization of the uniformity of dose to meet a value of 90 to 110%.

21. The process according to claim 14, comprising an optimization of the uniformity of dose to meet a value of 95 to 105%.

22. The process according to claim 14, comprising an optimization of the dose de-agglomeration (DD3 $\mu$m) for deep lung delivery to be more than 25%.

23. The process according to claim 14, comprising an optimization of the dose de-agglomeration (DD5 $\mu$m) for local lung delivery to be more than 25%.

24. The process according to claim 14, comprising an optimization of the pressure drop over the mouthpiece and the device member compared to a total pressure drop over the inhaler to be greater than 50%.

25. The process according to claim 14, comprising an optimization of a dissipative connection between the user and the DPI to eliminate electrical fields due to potential differences.

26. The process according to claim 14, comprising an adjustment of a dose delivery time in relation to a time for a user's full inspiration by an adjustment of a length of a dose powder strip on a dosing member to be used.

27. The method according to claim 1, comprising a definition of a dose delivery time $t_a$ to $T_a$ for a local lung delivery of said electro-powder and a dose delivery time $t_s$ to $T_s$ for a deep lung delivery of said electro-powder out of a total inhalation time period t to T, whereby $t_a>t_s$, $T_s>t_a$ and $T_a>T_s$ within a time span T–t.

28. The method according to claim 1, having electrical dissipative properties in contact with a user made out of dissipative or conductive polymers comprising a further step wherein electro-conductive material used is obtained from materials selected from the group of materials consisting of silver powder, platinum powder, gold powder, stainless steel powder, antimony-doped tin oxide, and antimony-doped silica oxide, or is an X-doped silica where X is an adamantine semiconductor or an octahedral semiconductor, and wherein the conductive material and the plastic material for a dissipative or conductive combination of the device member has a specification presenting a surface resistance of $10^3$–$10^{12}\Omega$, and a volume resistivity of $10^3$–$10^{12}$ ohm·m.

* * * * *